US012651147B2

(12) United States Patent
Smith et al.

(10) Patent No.: US 12,651,147 B2
(45) Date of Patent: Jun. 9, 2026

(54) SYSTEMS AND METHODS FOR TRAINING CONDITIONAL GENERATIVE MODELS

(71) Applicant: Unlearn.AI, Inc., San Francisco, CA (US)

(72) Inventors: Aaron Michael Smith, Corte Madera, CA (US); Charles Kenneth Fisher, Truckee, CA (US)

(73) Assignee: Unlearn.AI, Inc., San Francisco, CA (US)

( * ) Notice: Subject to any disclaimer, the term of this patent is extended or adjusted under 35 U.S.C. 154(b) by 21 days.

(21) Appl. No.: 18/448,843

(22) Filed: Aug. 11, 2023

(65) Prior Publication Data

US 2024/0169188 A1     May 23, 2024

Related U.S. Application Data

(63) Continuation of application No. 18/352,960, filed on Jul. 14, 2023.

(Continued)

(51) Int. Cl.
| | |
|---|---|
| *G06N 3/047* | (2023.01) |
| *G06N 3/0475* | (2023.01) |
| *G16H 10/20* | (2018.01) |

(52) U.S. Cl.
CPC ........... *G06N 3/047* (2023.01); *G06N 3/0475* (2023.01); *G16H 10/20* (2018.01)

(58) Field of Classification Search
None
See application file for complete search history.

(56) References Cited

U.S. PATENT DOCUMENTS

| | | | |
|---|---|---|---|
| 7,634,464 | B2 | 12/2009 | Chen et al. |
| 8,150,629 | B2 | 4/2012 | Geerts et al. |

(Continued)

FOREIGN PATENT DOCUMENTS

| | | |
|---|---|---|
| CA | 3088204 A1 | 7/2019 |
| CN | 111758108 A | 10/2020 |

(Continued)

OTHER PUBLICATIONS

Mnih et al., "Conditional Restricted Boltzmann Machines for Structured Output Prediction", (2012) (Year: 2012).*

(Continued)

*Primary Examiner* — Usmaan Saeed
*Assistant Examiner* — Beatriz Ramirez Bravo
(74) *Attorney, Agent, or Firm* — KPPB LLP

(57) ABSTRACT

Systems and techniques for adjusting experiment parameters are illustrated. One embodiment includes a method that defines a joint distribution, wherein the joint distribution corresponds to a combination of a probabilistic model and a point prediction model, and wherein the point prediction model is configured to obtain a measurement of regression accuracy. The method derives an energy function for the joint distribution. The method obtains, from the energy function for the joint distribution, an approximation for a conditional distribution, wherein an output of the point prediction model is a parameter of the approximation. The method determines, from a loss function, at least one training parameter. The method trains the probabilistic based on the at least one parameter to operate as a conditional generative model, wherein the trained probabilistic model follows the conditional distribution. The method applies the trained probabilistic model to a dataset corresponding to a randomized trial.

20 Claims, 7 Drawing Sheets

Related U.S. Application Data

(60) Provisional application No. 63/384,021, filed on Nov. 16, 2022.

(56) References Cited

U.S. PATENT DOCUMENTS

| | | | |
|---|---|---|---|
| 9,495,582 B2 | 11/2016 | Guissin et al. |
| 10,398,389 B1 | 9/2019 | D'Alessandro et al. |
| 10,650,929 B1 | 5/2020 | Beck et al. |
| 10,726,954 B2 | 7/2020 | Su et al. |
| 11,120,528 B1 | 9/2021 | Seely et al. |
| 11,196,656 B1 | 12/2021 | Jain et al. |
| 11,200,511 B1 | 12/2021 | London |
| 11,501,429 B2 | 11/2022 | Stamatoyannopoulos et al. |
| 11,574,462 B1 | 2/2023 | Bhatia et al. |
| 11,610,126 B1 | 3/2023 | Heckerman et al. |
| 11,636,309 B2 | 4/2023 | Fisher et al. |
| 11,868,900 B1 | 1/2024 | Smith et al. |
| 11,966,850 B1 | 4/2024 | Smith et al. |
| 12,008,478 B2 | 6/2024 | Smith et al. |
| 12,020,789 B1 | 6/2024 | D'Alessio et al. |
| 2004/0059696 A1 | 3/2004 | Kropaczek et al. |
| 2004/0193019 A1 | 9/2004 | Wei |
| 2005/0047646 A1 | 3/2005 | Jojic et al. |
| 2005/0080462 A1 | 4/2005 | Jenkins et al. |
| 2008/0082359 A1 | 4/2008 | Jung et al. |
| 2009/0326976 A1 | 12/2009 | Morris |
| 2010/0235310 A1 | 9/2010 | Gage et al. |
| 2010/0254973 A1 | 10/2010 | Mohapatra et al. |
| 2011/0116522 A1 | 5/2011 | Riggs et al. |
| 2011/0218817 A1 | 9/2011 | Spiegel |
| 2013/0311968 A1 | 11/2013 | Sharma |
| 2014/0019059 A1 | 1/2014 | Shankle et al. |
| 2014/0046683 A1 | 2/2014 | Michelson et al. |
| 2014/0257128 A1 | 9/2014 | Moxon et al. |
| 2014/0279777 A1 | 9/2014 | Cornebise et al. |
| 2015/0010610 A1 | 1/2015 | Tom et al. |
| 2015/0185716 A1 | 7/2015 | Wichmann et al. |
| 2016/0140300 A1 | 5/2016 | Purdie et al. |
| 2016/0180053 A1 | 6/2016 | Fuertinger et al. |
| 2016/0217384 A1 | 7/2016 | Leonard et al. |
| 2016/0222448 A1 | 8/2016 | Horvath |
| 2017/0091615 A1 | 3/2017 | Liu et al. |
| 2017/0161635 A1 | 6/2017 | Oono et al. |
| 2017/0255871 A1 | 9/2017 | Macready et al. |
| 2017/0286627 A1 | 10/2017 | Barhak |
| 2017/0316507 A1 | 11/2017 | Shah |
| 2017/0344706 A1 | 11/2017 | Torres et al. |
| 2017/0357844 A1 | 12/2017 | Comaniciu et al. |
| 2017/0364043 A1 | 12/2017 | Ganti et al. |
| 2017/0364803 A1 | 12/2017 | Calmon et al. |
| 2017/0372193 A1 | 12/2017 | Mailhe et al. |
| 2018/0018590 A1 | 1/2018 | Szeto et al. |
| 2018/0046780 A1 | 2/2018 | Graiver et al. |
| 2018/0081914 A1 | 3/2018 | Zoll et al. |
| 2018/0082172 A1 | 3/2018 | Patel et al. |
| 2018/0150728 A1 | 5/2018 | Vahdat |
| 2018/0204138 A1 | 7/2018 | Nugent |
| 2018/0299152 A1 | 10/2018 | Libal et al. |
| 2018/0314573 A1 | 11/2018 | Chang et al. |
| 2018/0315505 A1 | 11/2018 | Itu et al. |
| 2018/0316781 A1 | 11/2018 | Salem |
| 2018/0336319 A1 | 11/2018 | Itu et al. |
| 2019/0018933 A1 | 1/2019 | Oono et al. |
| 2019/0019570 A1 | 1/2019 | Fuertinger et al. |
| 2019/0130281 A1 | 5/2019 | Yang et al. |
| 2019/0220733 A1 | 7/2019 | Fisher et al. |
| 2019/0244680 A1 | 8/2019 | Rolfe et al. |
| 2019/0283247 A1 | 9/2019 | Chang et al. |
| 2019/0294990 A1 | 9/2019 | Lopez De Prado |
| 2019/0303471 A1 | 10/2019 | Lee et al. |
| 2019/0303798 A1 | 10/2019 | Xie et al. |
| 2020/0035362 A1 | 1/2020 | Abou Shousha et al. |
| 2020/0143498 A1 | 5/2020 | Alkan et al. |
| 2020/0357490 A1 | 11/2020 | Kartoun et al. |
| 2020/0395103 A1 | 12/2020 | Ramakrishnan et al. |
| 2020/0401916 A1 | 12/2020 | Rolfe et al. |
| 2020/0411199 A1 | 12/2020 | Shrager et al. |
| 2021/0057108 A1 | 2/2021 | Fisher et al. |
| 2021/0090694 A1 | 3/2021 | Colley et al. |
| 2021/0117842 A1 | 4/2021 | Smith et al. |
| 2021/0158906 A1 | 5/2021 | Xie et al. |
| 2021/0225511 A1* | 7/2021 | Kiraly ................... G16H 50/20 |
| 2021/0241139 A1 | 8/2021 | Jain et al. |
| 2021/0241860 A1 | 8/2021 | Bhattacharya et al. |
| 2021/0256453 A1 | 8/2021 | Morgan et al. |
| 2021/0353203 A1 | 11/2021 | Burman et al. |
| 2021/0383173 A1* | 12/2021 | Laaser ................. G06F 18/217 |
| 2021/0406740 A1 | 12/2021 | Patel et al. |
| 2022/0003894 A1 | 1/2022 | Shapiro et al. |
| 2022/0051796 A1 | 2/2022 | Zhu et al. |
| 2022/0121955 A1 | 4/2022 | Chavoshi et al. |
| 2022/0157413 A1* | 5/2022 | Fisher ................... G16H 20/10 |
| 2022/0172085 A1 | 6/2022 | Fisher et al. |
| 2022/0172638 A1* | 6/2022 | Aharonson ............ G09B 15/00 |
| 2022/0187776 A1 | 6/2022 | Bagne |
| 2022/0188601 A1 | 6/2022 | Adler et al. |
| 2022/0262106 A1* | 8/2022 | Khoreva ................ G06N 3/084 |
| 2022/0300329 A1 | 9/2022 | Abhishek Raja |
| 2022/0318689 A1 | 10/2022 | Li-Bland et al. |
| 2022/0344009 A1 | 10/2022 | Schuler da Costa Ferro |
| 2022/0410385 A1 | 12/2022 | Shimura |
| 2022/0415454 A1 | 12/2022 | Schuler da Costa Ferro et al. |
| 2023/0004796 A1 | 1/2023 | Mayer et al. |
| 2023/0094389 A1* | 3/2023 | You .......................... G06N 5/01 706/62 |
| 2023/0118864 A1 | 4/2023 | Zhang et al. |
| 2023/0209035 A1 | 6/2023 | Kaabi et al. |
| 2023/0245258 A1 | 8/2023 | Ma et al. |
| 2023/0245777 A1 | 8/2023 | Foschini et al. |
| 2024/0013525 A1* | 1/2024 | Lim ....................... G06N 3/045 |
| 2024/0169187 A1 | 5/2024 | Smith et al. |
| 2024/0303493 A1 | 9/2024 | Smith et al. |
| 2025/0022556 A1 | 1/2025 | D'alessio et al. |

FOREIGN PATENT DOCUMENTS

| | | | |
|---|---|---|---|
| CN | 112863622 A | 5/2021 |
| CN | 113724806 A | 11/2021 |
| EP | 3740908 A1 | 11/2020 |
| EP | 4018394 A1 | 6/2022 |
| EP | 4220650 A1 | 8/2023 |
| EP | 4256418 A2 | 10/2023 |
| HK | 40098681 A | 4/2024 |
| JP | 2021511584 A | 5/2021 |
| JP | 202231730 A | 2/2022 |
| JP | 2022544859 A | 10/2022 |
| JP | 7305656 B2 | 6/2023 |
| JP | 2023551514 A | 12/2023 |
| WO | 0229556 A2 | 4/2002 |
| WO | 2006084196 A2 | 8/2006 |
| WO | 2007022020 A2 | 2/2007 |
| WO | 2007022020 A3 | 6/2007 |
| WO | 2014114295 A1 | 7/2014 |
| WO | 2016145379 A1 | 9/2016 |
| WO | 2019143737 A1 | 7/2019 |
| WO | 2020115487 A1 | 6/2020 |
| WO | 2020154573 A1 | 7/2020 |
| WO | 2021041128 A1 | 3/2021 |
| WO | 2021077097 A1 | 4/2021 |
| WO | 2022003528 A1 | 1/2022 |
| WO | 2022101809 A1 | 5/2022 |
| WO | 2022120350 A2 | 6/2022 |
| WO | 2022125806 A1 | 6/2022 |
| WO | 2022120350 A3 | 8/2022 |
| WO | 2022187064 A1 | 9/2022 |
| WO | 202221425 A1 | 10/2022 |
| WO | 2022261420 A1 | 12/2022 |
| WO | 2022272308 A1 | 12/2022 |
| WO | 2019143737 A8 | 3/2023 |

(56) References Cited

FOREIGN PATENT DOCUMENTS

| WO | 2024107461 A1 | 5/2024 |
|----|---------------|--------|
| WO | 2024172853 A1 | 8/2024 |

OTHER PUBLICATIONS

Luo et al., "Texture Modeling with Convolutional Spike-and-Slab RBMs and Deep Extensions" (2013) (Year: 2013).*
Upadhya et al., "Learning Gaussian-Bernoulli RBMs Using Difference of Convex Functions Optimization" (2021) (Year: 2021).*
Takayuki, "Boltzmann machines for time-series", IBM Research—Tokio (2019) (Year: 2019).*
Mandel et al., "Autotagging music with conditional restricted Boltzmann machines", (2011) (Year: 2011).*
Extended European Search Report for European Application No. 19741291.9, Search completed Sep. 8, 2021, Mailed Sep. 17, 2021, 12 pgs.
Extended European Search Report for European Application No. 20857028.3, Search completed Aug. 11, 2023, Mailed Aug. 21, 2023, 12 pgs.
Extended European Search Report for European Application No. 23154548.4, Search completed Jun. 15, 2023, Mailed Jun. 23, 2023, 11 pgs.
International Preliminary Report on Patentability for International Application PCT/US2019/013870 Report issued Jul. 21, 2020, Mailed Jul. 30, 2020, 5 pgs.
International Preliminary Report on Patentability for International Application PCT/US2020/047054, Report issued Feb. 17, 2022, Mailed on Mar. 3, 2022, 6 pgs.
International Preliminary Report on Patentability for International Application PCT/US2020/056354, Report issued Apr. 19, 2022, Mailed on Apr. 28, 2022, 6 pgs.
International Preliminary Report on Patentability for International Application PCT/US2021/072678, Report issued May 30, 2023, Mailed on Jun. 15, 2023, 9 pgs.
International Search Report and Written Opinion for International Application No. PCT/US2019/013870, Search completed Mar. 18, 2019, Mailed Mar. 27, 2019, 9 pgs.
International Search Report and Written Opinion for International Application No. PCT/US2020/047054, Search completed Oct. 8, 2020, Mailed Nov. 23, 2020, 10 pgs.
International Search Report and Written Opinion for International Application No. PCT/US2020/056354, Search completed Dec. 21, 2020, Mailed Jan. 25, 2021, 09 pgs.
International Search Report and Written Opinion for International Application No. PCT/US2022/073165, Search completed Aug. 14, 2022, Mailed Sep. 7, 2022, 9 pgs.
International Search Report and Written Opinion for International Application No. PCT/US2023/069016, Search completed Sep. 18, 2023, Mailed Oct. 18, 2023, 11 pgs.
International Search Report and Written Opinion for International Application No. PCT/US2023/070276, Search completed Oct. 6, 2023, Mailed Nov. 8, 2023, 16 pgs.
International Search Report and Written Opinion for International Application PCT/US2021/072678, search completed Jan. 31, 2022, Mailed Jul. 1, 2022, 13 pgs.
"Procova™ Handbook for the Target Trial Statistician", Ver. 1.0, European Medicines Agency, Dec. 29, 2021, 7 pgs.
Ackley et al., "A learning algorithm for boltzmann machines", Cognitive Science, vol. 9, No. 1, 1985, pp. 147-169.
Akhtar et al., "Improving the Robustness of Neural Networks Using K-Support Norm Based Adversarial Training", IEEE Access; Publication [online]. Dec. 28, 2016, 10 pgs.
Allison, et al., "Handling Missing Data by Maximum Likelihood", SAS Global Forum 2012: Statistics and Data Analysis, 21 pgs.
Amin et al., "Quantum Boltzmann Machine", [retrieved on Jun. 10, 2023]. Retrieved from the Internet: <URL:https://journals.aps.org/prx/pdf/10.1103/PhysRevX.8.021050>, May 23, 2018, pp. 021050-1 to 021050-11.

Arici et al., "Associative Adversarial Networks", arXiv:1611.06953v1 [cs.LG], Nov. 18, 2016, 8 pgs. URL:https://arxiv.org/abs/1611. 06953.
Arjovsky et al., "Wasserstein GAN", arXiv:1701.07875v1 [stat.ML], Jan. 26, 2017, 30 pgs.
Arjovsky et al., "Wasserstein Generative Adversarial Networks", Proceedings of the 34th International Conference on Machine Learning, 2017, pp. 214-223.
Balzer et al., "Adaptive pair-matching in randomized trials with unbiased and efficient effect estimation", Statistics in Medicine, 2015, vol. 34, pp. 999-1011.
Bengio, et al., "Greedy Layer-Wise Training of Deep Networks", Advances in Neural Information Processing Systems, 2007, 13 pgs.
Burges et al., "Learning to Rank Using Gradient Descent", Proceedings of the 22nd International Conference on Machine Learning, 2005, 8 pgs.
Chatterjee et al., "Explaining Complex Distributions with Simple Models", 2008. Econophysics. pp. 1-15.
Cho et al., "Gaussian-Bernoulli deep Boltzmann machine", Proceedings of the 2013 International Joint Conference on Neural Networks (IJCNN), Dallas, Texas, Aug. 4-9, 2013, 9 pgs.
Coon et al., "A High-Density Whole-Genome Association Study Reveals That APOE Is the Major Susceptibility Gene for Sporadic Late-Onset Alzheimer's Disease", The Journal of Clinical Psychiatry, 2007, vol. 68, No. 04, 2007, 14 pgs., doi: 10.4088/jcp.v68n0419.
Cui et al., "Multilevel Modeling and Value of Information in Clinical Trial Decision Support", BMC Systems Biology, vol. 8, No. 6, 2014, 8 pgs., DOI 10.1186/s12918-014-0140-0.
Leon et al., "Semiparametric Estimation of Treatment Effect in a Pretest-Posttest Study", Biometrics, Dec. 2003, vol. 59, No. 4, 2003, pp. 1046-1055, ISSN 0006-341X. doi: 10.1111/ j.0006-341x.2003.00120.x.
Duan et al., "Utilizing dynamic treatment information for MACE prediction of acute coronary syndrome", BMC Medical Informatics and Decision Making, 2019, pp. 1-11.
Dutt et al., "Generative Adversarial Networks (GAN) Review", CVR Journal of Science and Technology, Dec. 2017, vol. 13, pp. 1-5.
Eickhoff et al., "Copulas for Information Retrieval", Proceedings of the 36th International ACM SIGIR Conference on Research and Development in Information Retrieval, Jul. 2013, pp. 663-672.
Fisher et al., "Boltzmann Encoded Adversarial Machines", arxiv.org:1804.08682v1, Apr. 23, 2018, XP081229135, 17 pgs.
Fisher et al., "Machine learning for comprehensive forecasting of Alzheimers disease progression", Scientific Reports, vol. 9, No. 1, 2019, pp. 1-14.
Fisher et al., "Machine Learning for Comprehensive Forecasting of Alzheimer's Disease Progression", Sep. 20, 2019, Scientific Reports, pp. 1-41. (with Supporting Information, Year: 2019).
Gabrie et al., "Training Restricted Boltzmann Machines via the Thouless-Anderson-Palmer Free Energy", Advances in Neural Information PRocessing Systems, vol. 28, 2015, 9 pgs.
Ghojogh et al., "Restricted Boltzmann Machine and Deep Belief Network: Tutorial and Survey", arXiv preprint arXiv:2107.12521, 2022, 16 pgs.
Goodfellow et al., "Generative Adversarial Nets", arXiv:1406.2661v1 [stat.ML], Jun. 10, 2014, 9 pgs.
Goodfellow et al., "Multi-Prediction Deep Boltzmann Machines", [retrieved on Jun. 10, 2023]. Retrieved from the Internet: <URL:https://proceedings.neurips.cc/paper/2013/file/0bb4aec1710521c12ee76289d9440817-Paper.pdf> Dec. 5, 2013, pp. 1-9.
Graham et al., "Analysis with missing data in drug prevention research", NIDA Research Monograph, Feb. 1994, vol. 142, pp. 325-366.
Greydanus, "Generative Adversarial Networks for the MNIST dataset", "Mnist gan," http://github.com/greydanus/mnist-gan (2017), 2 pgs.
Grover et al., "Flow-GAN: Combining Maximum Likelihood and Adversarial Learning in Generative Models", arXiv:1705.08868v2, Jan. 3, 2018, 10 pgs.
Gupta, "Intention-to-treat concept: a review", Perspectives in Clinical Research, Jul. 2011, vol. 2, No. 3, pp. 109-112, doi: 10.4103/2229-3485.83221.

(56)          References Cited

OTHER PUBLICATIONS

Hannan, "Randomized Clinical Trials and Observational Studies: Guidelines for Assessing Respective Strengths and Limitations", JACC: Cardiovascular Interventions, Jun. 2008, vol. 1, No. 3, pp. 211-217, https://doi.org/10.1016/j.jcin.2008.01.008.

Herlau et al., "Bayesian Dropout", arXiv e-prints (2015): arXiv-1508.02905v1, 21 pgs.

Hinton, "A Practical Guide to Training Restricted Boltzmann Machines", Neural networks: Tricks of the trade, pp. 599-619. Springer, Berlin, Heidelberg, 2012.

Hinton et al., "A Fast Learning Algorithm for Deep Belief Nets", Neural Computation 18, pp. 1527-1554 (2006).

Hinton et al., "Reducing the Dimensionality of Data with Neural Networks" Science, vol. 313, No. 5786, Jul. 28, 2006, pp. 504-507.

Hinton et al., "Training products of experts by minimizing contrastive divergence", Neural Computation, vol. 14, No. 8, 2002, pp. 1771-1800.

Hoffman et al., "Training Compute-Optimal Large Language Models", arXiv preprint arXiv:2203.15556, 2022, 36 pgs.

Jerez et al., "Missing data imputation using statistical and machine learning methods in a real breast cancer problem", Artificial Intelligence in Medicine, (Year: 2010), vol. 50, Issue 2, pp. 105-115.

Karcher et al., "The "RCT augmentation": a novel simulation method to add patient heterogeneity into phase III trials", BMC Medical Research Methodology, vol. 18, No. 75, 2018, pp. 1-14, https://doi.org/10.1186/s1287 4-018-0534-6.

Kim et al., "Deep Directed Generative Models with Energy-Based Probability Estimation", arXiv:1606.03439, Jun. 10, 2016, 9 pages. <URL: https : //arxiv.org/abs/1606. 03439>.

Kullback et al., "On Information and Sufficiency", The Annals of Mathematical Statistics, vol. 22, No. 1, 1951, pp. 79-86.

Lamb et al., "GibbsNet: Iterative Adversarial Inference for Deep Graphical Models", arXiv preprint arXiv:1712.04120v1, 2017, 11 pgs.

Li et al., "Temperature based Restricted Boltzmann Machines", Scientific Reports Jan. 13, 2016, vol. 6, No. 19133, 12 pgs., DOI:10.1038/srep19133.

Liao et al., "Gaussian-Bernoulli RBMs Without Tears", arXiv preprint arXiv:2210.10318, 2022, 18 pgs.

Lim et al., "Time-Series Forecasting with Deep Learning: A Survey", Jul. 28, 2021, The Royal Society Publishing, pp. 1-14 (Year: 2021).

Lipton et al., "Modeling Missing Data in Clinical Time Series with RNNs", Machine Learning for Healthcare. Jun. 13, 2016, vol. 56, 17 pgs.

Liu et al., "A Survey of Deep Neural Network Architectures and their Applications", Neurocomputing, Apr. 19, 2017, vol. 234, pp. 11-26, XP029916222, ISSN: 0925-2312, DOI: 10.1016/J.NEUCOM. 2016.12.038.

Liu et al., "Image inpainting for irregular holes using partial convolutions", Image Inpainting for Irregular Holes Using Partial Convolutions, Proceedings of the European conference on computer vision (ECCV), arXiv:1804.07723, 2018, 23 pgs.

Lopez-Ruiz et al., "Equiprobability, Entropy, Gamma Distributions and Other Geometrical Questions in Multi-Agent Systems", Entropy, 2009, vol. 11, pp. 959-971, doi: 10.3390/e11040959.

Maldonado, "Estimating causal effects", International Journal of Epidemiology, Apr. 2002, vol. 31, No. 2, pp. 422-429.

Mandel et al., "Autotagging music with conditional restricted Boltzmann machines", arXiv:1103.2832; (Year: 2011), https://doi.org/10.48550/arXiv.1103.2832, 14 pgs.

Marlin et al., "Recommender systems: Missing Data and statistical Model Estimation", Proceedings of the Twenty-Second international joint conference on Artificial Intelligence, 2011, vol. Three (IJCAI'11), AAAI Press, pp. 2686-2691.

Melchior et al., "Gaussian-Binary Restricted Boltzmann Machines for Modeling Natural Image Statistics", PLOS ONE, vol. 12, No. 2, 2017, pp. 1-24.

Miotto et al., "Deep Learning for Healthcare: Review, Opportunities and Challenges", Briefings in Bioinformatics, May 6, 2017 (May 6, 2017), vol. 19, No. 6, pp. 1236-1246, GB ISSN: 1467-5463, DOI: 10.1093/bib/bbx044.

Mnih et al., "Conditional Restricted Boltzmann Machines for Structured Output Prediction", arXiv preprint arXiv:1202.3748, 2012, 9 pgs.

Montavon et al., "Wasserstein Training of Restricted Boltzmann Machines", Advances in Neural Information Processing Systems, vol. 29, 2016, 9 pgs.

Nakkiran et al., "Deep Double Descent: Where Bigger Models and More Data Hurt", arXiv preprint, arXiv:1912.02292, 2019, 24 pgs.

Neville et al., "Development of a unified clinical trial database for Alzheimer's disease", Alzheimer's & Dementia: The Journal of the Alzheimer's Association, 2015, vol. 11, No. 10, pp. 1212-1221, https://doi.org/10.1016/j.jalz.2014.11.005.

Nguyen et al., "Latent Patient Profile Modelling and Applications with Mixed-Variate Restricted Boltzmann Machine", Advances in Knowledge Discovery and Data Mining, 2013, pp. 123-135.

Nguyen et al., "Supervised Restricted Boltzmann Machines", UAI. 2017, 10 pgs.

Niu et al., "A review on the attention mechanism of deep learning", Neurocomputing, vol. 452, 2021, pp. 48-62, https://doi.org/10.1016/j.neucom.2021.03.091.

OpenAI, "Gpt-4 technical report", arXiv preprint arXiv:2303.08774, 2023, 100 pgs.

Overhage et al., "Desideratum for evidence based epidemiology", Drug Safety, 2013, vol. 36, Suppl. 1, pp. S5-S14, DOI: 10.1007/s40264-013-0102-2.

Quinn et al., "Docosahexaenoic Acid Supplementation and Cognitive Decline in Alzheimer Disease: A Randomized Trial", Journal of the American Medical Association, Nov. 3, 2010, vol. 304, No. 17, pp. 1903-1911, doi: 10.1001/jama.2010.1510.

Rogers et al., "Combining patient-level and summary-level data for Alzheimer's disease modeling and simulation: a beta regression meta-analysis", Journal of Pharmacokinetics and Pharmacodynamics, vol. 39, 2012, pp. 479-498.

Romano et al., "Resurrecting weighted least squares", Journal of Econometrics, vol. 197, No. 1, 48 pgs., Available at: https://doi.org/10.1016/j.jeconom.2016.10.003.

Rombach et al., "High-Resolution Image Synthesis with Latent Diffusion Models", arXiv preprint arXiv:2112.10752, 2022, 45 pgs.

Romero et al., "The coalition against major diseases: developing tools for an integrated drug development process for alzheimer's and parkinson's diseases", Clinical Pharmacology & Therapeutics, Aug. 12, 2009, vol. 86, No. 4, pp. 365-367, https://doi.org/10.1038/clpt.2009.165.

Rosen et al., "A New Rating Scale for Alzheimer's Disease", American Journal of Psychiatry, Nov. 1984, vol. 141, Issue 11, pp. 1356-1364, https://doi.org/10.1176/ajp.141.11.1356.

Royston, "A Combined Test for a Generalized Treatment Effect in Clinical Trials with a Time-to-Event Outcome", The Stata Journal, vol. 17, No. 2, 2017, pp. 405-421.

Royston et al., "A Simulation Study Comparing the Power of Nine Tests of the Treatment Effect in Randomized Controlled Trials with a Time-to-Event Outcome", Royston and Parmar Trials (2020). Retrieved on Aug. 14, 2022. vol. 21, No. 315, 17 pgs. Retrieved from <URL: https://link.springer.com/content/pdf/10.1186/s13063-020-4153-2.pdf> entire document.

Royston et al., "Augmenting the Logrank Test in the Design of Clinical Trials in which Non-Proportional Hazards of the Treatment Effect may be Anticipated", Royston and Parmar BMC Medical Research Methodology, vol. 16, No. 16, 2016, 13 pages. Retrieved on Aug. 14, 2022. Retrieved from <URL:https://bmcmedresmethodol. biomedcentral.conn/track/pdf/10.1186/s12874-016-0110-x.pdf> entire document.

Rubin, "Causal Inference Using Potential Outcomes: Design, Modeling, Decisions", Journal of the American Statistical Association, vol. 100, No. 469, Mar. 2005, pp. 322-331, https://doi.org/10.1198/016214504000001880.

Saharia et al., "Photorealistic text-to-image diffusion models with deep language understanding", arXiv preprint arXiv:2205.11487, 2022, 46 pgs.

(56)         References Cited

OTHER PUBLICATIONS

Salakhutdinov et al., "Deep Boltzmann Machines", Proc. International Conference on Artificial Intelligence and Statistics, 2009, pp. 448-455.

Schuler et al., "Increasing the efficiency of randomized trial estimates via Linear Adjustment for a prognostic score", The International Journal of Biostatistics, vol. 18, No. 2, pp. 329-356. Available at: https://doi.org/10.1515/ijb-2021-0072.

Shan et al., "Accurate Unconditional p-Values for a Two-Arm Study with Binary Endpoints", Journal of Statistical Computation and Simulation, [Online] Apr. 13, 2018, vol. 88, No. 6, pp. 1200-1210, XP093073190, ISSN: 0094-9655, DOI: 10.1080/00949655.2018. 1425690, Retrieved from the Internet: URL:https://www.ncbi.nlm. nih.gov/pmc/artic les/PMC6510515/pdf/nihms-1504617.pdf> [retrieved on Jan. 28, 2018].

Shan et al., "Exact p-Values for Simon's Two-Stage Designs in Clinical Trials", Statistics in Biosciences, Springer US, Boston, [Online]Jun. 16, 2016, vol. 8, No. 2, pp. 351-357, XP036062971,ISSN: 1867-1764, DOI:10.1007/S12561-016- 9152-1, Retrieved from the Internet: URL:https://www.ncbi.nlm.nih.gov/pmc/articles/PMC5167475/ >.

Silva et al., "Predicting In-Hospital Mortality of ICU Patients: The PhysioNet/Computing in Cardiology Challenge 2012", Computing in Cardiology, 2012, vol. 39, pp. 245-248.

Sohl-Dickstein et al., "Deep Unsupervised Learning using Nonequilibrium Thermodynamics", arXiv preprint arXiv:1503. 03585, 2015, 18 pgs.

Song et al., "Generative Adversarial Learning of Markov Chains", Accessed at URL https://openreview.net/forum?id=S1L-hCNtl, 2017, 8 pgs.

Sox et al., "The Methods of Comparative Effectiveness Research", Annual Review of Public Health, Apr. 2012, vol. 33, pp. 425-445, doi: 10.1146/annurev-publhealth-031811-124610.

Sterne et al., "Multiple imputation for missing data in epidemiological and clinical research: potential and pitfalls", BMJ, 2009, 14 pages, doi: https://doi.org/10.1136/bmj.b2393 (Published Jun. 29, 2009).

Sutskever et al., "The Recurrent Temporal Restricted Boltzmann Machine", Advances in Neural Information Processing Systems, 2009, pp. 1601-1608.

Takayuki, "Boltzmann Machines for Time-Series", IBM Research—Tokio; 2019; arXiv:1708.06004v3 [cs.NE], 33 pgs.

Tan et al., "A tensor-based method for missing traffic data completion", Transportation Research Part C: Emerging Technologies, vol. 28, 2013, pp. 15-27, https://doi.org/10.1016/j.trc.2012.12.007.

Taylor et al., "Factored conditional restricted boltzmann machines for modeling motion style", In Proceedings of the 26th Annual International Conference on Machine Learning, Association for Computing Machinery, 2009, pp. 1025-1032.

Taylor et al., "Modeling human motion using binary latent variables", In Advances in Neural Information Processing Systems, pp. 1345-1352, 2007.

Tieleman, "Training restricted boltzmann machines using approximations to the likelihood gradient", In Proceedings of the 25th international conference on Machine learning, ACM, 2008, pp. 1064-1071.

Tipirneni et al., "Self-supervised transformer for sparse and irregularly sampled multivariate clinical time-series", ACM Transactions on Knowledge Discovery from Data (TKDD), 2022, vol. 1, No. 1, 18 pgs.

Tran et al., "Mixed-Variate Restricted Boltzmann Machines", Asian Conference on Machine Learning, JMLR: Workshop and Conference Proceedings 20, 2011, pp. 213-229.

Tuzman, "Broadening role for external control arms in clinical trials", Biocentury, Tools & Techniques, reprint from Jul. 15, 2019, 5 pgs.

Upadhya et al., "Learning Gaussian-Bernoulli RBMs using Difference of Convex Functions Optimization", IEEE Transactions on Neural Networks and Learning Systems, vol. 33, No. 10, 2022, pp. 1-24.

Vaswani et al., "Attention Is All You Need", arXiv preprint arXiv:1706. 03762, 2023, 15 pgs.

Ventz et al., "Design and Evaluation of an External Control Arm Using Prior Clinical Trials and Real-World Data", Clincal Cancer Resarch 2019; 25:4993-5001; doi: 10.1158/1078-0432.CCR-19-0820.

Yi et al., "ST-MVL: Filling Missing Values in Geo-Sensory Time Series Data", Proceedings of the Twenty-Fifth International Joint Conference on Artificial Intelligence, 2016, pp. 2704-2710.

Yu et al., "Assessment and adjustment of approximate inference algorithms using the law of total variance", arXiv preprint arXiv:1911. 08725, Nov. 2019 [online], [retrieved on Jan. 31, 2022], 29 pgs.

Zhang et al., "Predictive Deep Boltzmann Machine for Multiperiod Wind Speed Forecasting", IEEE Transactions on Sustainable Energy, 2015, vol. 6, Issue 4, pp. 1416-1425, doi: 10.31109/TSTE.2015. 244387.

Zhu et al., "Physics-Constrained Deep Learning for High-dimensional Surrogate Modeling and Uncertainty Quantification without Labeled Data", arXiv preprint arXiv:1901.06314, 2019, 51 pgs.

Extended European Search Report for European Application No. 21901649.0, Search completed Dec. 5, 2024, Mailed Dec. 13, 2024, 09 Pgs.

International Preliminary Report on Patentability for International Application PCT/US2023/069016, Report issued Aug. 15, 2025, Mailed Aug. 28, 2025, 5 Pgs.

International Preliminary Report on Patentability for International Application PCT/US2023/070276, Report issued Apr. 29, 2025, Mailed May 30, 2025, 9 Pgs.

Gheyas et al., "A Neural Network-Based Framework for the Reconstruction of Incomplete Data Sets", Neurocomputing, vol. 73, No. 16-18,Oct. 1, 2010, pp. 3039-3065, ARXIV, XP027427058, doi: 10.1016/J.NEUCOM.2010.06.021.

Schomaker et al., "Bootstrap Inference when Using Multiple Imputation", Statistics in Medicine, arxiv.org, Cornell University Library, 201, Olin Library Cornell University Ithaca, NY, 14853, Feb. 25, 2016, vol. 37, No. 14, pp. 2252-2266, XP081153550, doi: 10.1002/ SIM.7654.

* cited by examiner

SYSTEMS AND METHODS FOR TRAINING CONDITIONAL GENERATIVE MODELS

CROSS-REFERENCE TO RELATED APPLICATIONS

The present invention is a continuation of U.S. patent application Ser. No. 18/352,960, titled "Systems and Methods for Supplementing Data With Generative Models," filed Jul. 14, 2023, which claims priority to U.S. Provisional Patent Application No. 63/384,021, titled "Systems and Methods for Training Conditional Generative Models," filed Nov. 16, 2022, the disclosures for which are incorporated herein by reference in their entireties.

FIELD OF THE INVENTION

The present invention generally relates to supplementing data for analysis and, more specifically, to training or adapting generative conditional generative models to supplement data for analysis.

BACKGROUND

In a world of uncertainty, it is difficult to properly model probability distributions across multiple dimensions based on diverse and heterogeneous data sets. For example, in the health industry, individual health outcomes are never certain. The condition of one patient with a disease may deteriorate rapidly, while another patient quickly recovers. The inherent stochasticity of individual health outcomes implies that health informatics must aim to predict health risks rather than deterministic outcomes. The ability to quantify and predict health risks has important implications for business models that depend on the health of a population. As such, generative models can be trained to generate potential outcome data based on characteristics of entities from individuals to entire populations.

Generative models are a class of machine learning models that learns to sample from, potentially multivariate and/or time-dependent, probability distributions that are consistent with the observed data. Generative models have various applications in a variety of additional fields, such as economic forecasting, climate modeling, and medical research. There are a variety of instances in which it is important to obtain information surrounding outcomes that are conditional on sets of pre-determined features, by modeling the entire (conditional) probability distributions. These models, generally applied to classification or regression, are usually called discriminative or conditional generative models.

SUMMARY OF THE INVENTION

Systems and techniques for adjusting experiment parameters are illustrated. One embodiment includes a method for training a conditional generative model. The method defines a joint distribution, wherein the joint distribution corresponds to a combination of a probabilistic model and a point prediction model, and wherein the point prediction model is configured to obtain a measurement of regression accuracy. The method derives an energy function for the joint distribution. The method obtains, from the energy function for the joint distribution, an approximation for a conditional distribution, wherein an output of the point prediction model is a parameter of the approximation. The method determines, from a loss function, at least one training parameter. The method trains the combination based on the at least one parameter to operate as a conditional generative model, wherein the conditional generative model follows the conditional distribution. The method applies the trained probabilistic model to a dataset corresponding to a randomized trial.

In a further embodiment, the probabilistic model is a conditional restricted Boltzmann machine (CRBM).

In a further embodiment, applying the trained probabilistic model to a dataset corresponding to a randomized trial includes using the CRBM to generate a set of samples of a target population.

In a still further embodiment, the joint distribution is represented as: $p(y, h|x)=Z^{-1}(x)e^{-U(y,h|x)}$, wherein y represents visible units of the CRBM, h represents hidden units of the CRBM, x represents feature units of the CRBM, Z(x) represents a normalization constant, and U(y, h|x) is the energy function; and wherein the normalization constant is represented as: $Z(x)=\int dy\Sigma_H e^{-U(y,h|x)}$.

In a further embodiment, the combination is trained by using gradient descent.

In another further embodiment, deriving, from the joint distribution, the energy function for the probabilistic model includes summing over states of hidden units of the CRBM.

In another embodiment, the measurement of regression accuracy is a minimum mean squared error prediction.

In still another embodiment, the approximation is a Laplace approximation.

In another embodiment, the mode of the conditional distribution is identified by the point prediction model; and the point prediction model includes at least one selected from the group consisting of a linear model, a neural network, a decision tree, and a differential model.

In still another embodiment, the loss function is a negative log-likelihood function.

One embodiment includes a non-transitory computer-readable medium for training a conditional generative model, wherein the program instructions are executable by one or more processors to perform a process. The process defines a joint distribution, wherein the joint distribution corresponds to a combination of a probabilistic model and a point prediction model, and wherein the point prediction model is configured to obtain a measurement of regression accuracy. The process derives an energy function for the joint distribution. The process obtains, from the energy function for the joint distribution, an approximation for a conditional distribution, wherein an output of the point prediction model is a parameter of the approximation. The process determines, from a loss function, at least one training parameter. The process trains the combination based on the at least one parameter to operate as a conditional generative model, wherein the conditional generative model follows the conditional distribution. The process applies the trained probabilistic model to a dataset corresponding to a randomized trial.

In a further embodiment, the probabilistic model is a conditional restricted Boltzmann machine (CRBM).

In a further embodiment, applying the trained probabilistic model to a dataset corresponding to a randomized trial includes using the CRBM to generate a set of samples of a target population.

In a still further embodiment, the joint distribution is represented as: $p(y, h|x)=Z^{-1}(x)e^{-U(y,h|x)}$, wherein y represents visible units of the CRBM, h represents hidden units of the CRBM, x represents feature units of the CRBM, Z(x) represents a normalization constant, and U(y, h|x) is the energy function; and wherein the normalization constant is represented as: $Z(x)=\int dy\Sigma_H e^{-U(y,h|x)}$.

In a further embodiment, the combination is trained by using gradient descent.

In another further embodiment, deriving, from the joint distribution, the energy function for the probabilistic model includes summing over states of hidden units of the CRBM.

In another embodiment, the measurement of regression accuracy is a minimum mean squared error prediction.

In still another embodiment, the approximation is a Laplace approximation.

In another embodiment, the mode of the conditional distribution is identified by the point prediction model; and the point prediction model includes at least one selected from the group consisting of a linear model, a neural network, a decision tree, and a differential model.
In still another embodiment, the loss function is a negative log-likelihood function.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Figure 1B:
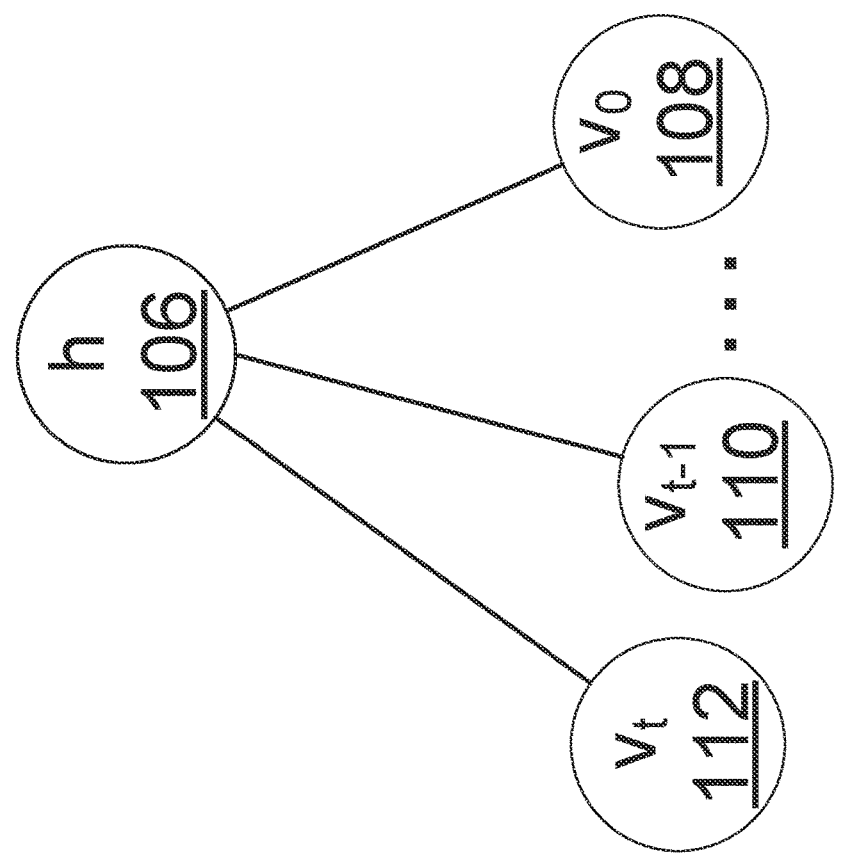
FIGS. 1A-1C illustrate machine learning models that may be used to implement unsupervised learning processes in accordance with many embodiments of the invention.

Systems and methods configured in accordance with some embodiments of the invention may produce conditional generative models by combining two or more machine learning models. In accordance with many embodiments of the invention, preliminary point prediction models may be applied to produce expected values for the outcome y given the features x. In doing so, secondary, probabilistic, models including but not limited to Conditional Restricted Boltzmann Machines (CRBMs) may be applied to further determine the corresponding distribution through describing the variability around the point prediction models. In accordance with many embodiments, untrained point prediction models can be combined with probabilistic models while the two models are trained simultaneously. Additionally or alternatively, the combined machine learning models may be used to refine time-series.

Machine learning is one potential approach to modeling complex probability distributions. In the following description, many examples are described with reference to medical applications, but one skilled in the art will recognize that techniques described herein can be readily applied in a variety of different fields including (but not limited to) health informatics, image/audio processing, marketing, sociology, and lab research. One of the most pressing problems is that one often has little, or no, labeled data that directly addresses a particular question of interest. Consider the task of predicting how a patient will respond to an investigational therapeutic in a clinical trial. In a supervised learning setting, one would give the therapeutic to many patients and observe how each patient responds. Then, one would use this data to build a model that predicts how a new patient will respond to the therapeutic. For example, a nearest neighbor classifier would look through the pool of previously treated patients to find a patient that is most similar to the new patient, then it would predict the new patient's response based on the previously treated patient's response. However, supervised learning requires significant amounts of labeled data and, particularly where sample sizes are small or labeled data is not readily available, unsupervised learning is critical to the successful application of machine learning.

Many machine learning applications, such as computer vision, require the use of homogeneous information (e.g., images of the same shape and resolution), which must be pre-processed or otherwise manipulated to normalize the input and training data. However, in many applications, it is desirable to combine data of various types (e.g., images, numbers, categories, ranges, text samples, etc.) from many sources. For example, medical data can include a variety of different types of information from a variety of different sources, including (but not limited to) demographic information (e.g., a patient's age, ethnicity, etc.), diagnoses (e.g., binary codes that describe whether or not a patient has a particular disease), laboratory values (e.g., results from laboratory tests, such as blood tests), doctor's notes (e.g., handwritten notes taken by a physician or entered into a medical records system), images (e.g., x-rays, CT scans, MRIs, etc.), and 'omics data (e.g., data from DNA sequencing studies that describe a patient's genetic background, the expression of his/her genes, etc.). Some of these data are binary, some are continuous, and some are categorical. Integrating all of these different types and sources of data is critical, but treating a variety of data types with traditional approaches to machine learning is quite challenging. Typically, the data have to be heavily pre-processed so that all of the features used for machine learning are of the same type. Data pre-processing steps can take up a large portion of an analyst's time in training and implementing a machine learning model.

Many embodiments of the invention provide novel and innovative systems and methods for the use of heterogeneous, irregular, and unlabeled data to train and implement stochastic, unsupervised machine-learning models of complex probability distributions.
Boltzmann Machine Architectures With many traditional machine learning techniques, supervised learning is used to train a model on a large set of labeled data to make predictions and classifications. However, in many cases, it is not feasible or possible to gather such large samples of labeled data. In many cases, the data cannot be readily labeled or there are simply not enough samples of an event to meaningfully train a supervised learning model. For example, clinical trials often face difficulties in gathering such labeled data. A clinical trial typically proceeds through three main phases. In phase I, the therapeutic is given to healthy volunteers to assess its safety. In phase II, the therapeutic is given to approximately 100 patients to obtain initial estimates for safety and efficacy. Finally, in phase III, the therapeutic is given to a few hundred to a few thousand patients to rigorously investigate the efficacy of the drug. Before phase II, there is no in-human data on the effect of the investigational drug for the desired indication, making supervised learning impossible. After phase II, there is some in-human data on the effect of the investigational drug, but the sample size is quite limited, rendering supervised learning techniques ineffective. For comparison, a phase II clinical trial may have 100-200 patients, whereas a typical application of machine learning in computer vision may use millions of labeled images. As with many situations with limited data, the lack of large labeled datasets for many important problems implies that health informatics must heavily rely on methods for unsupervised learning.

1. Restricted Boltzmann Machines (RBMs)

Figure 1A:
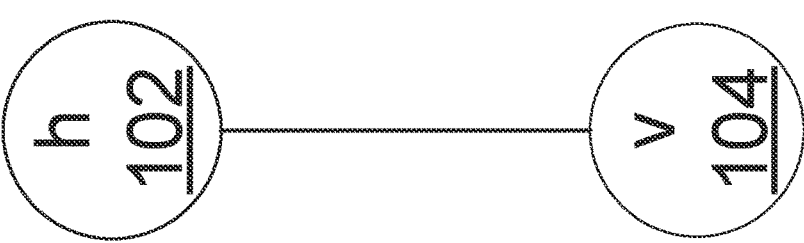
Figure 1C:

FIGS. 1A-1C illustrate machine learning models that may be used to implement unsupervised learning processes in accordance with many embodiments of the invention. Such models may include but are not limited to Restricted Boltzmann Machines (RBMs), as illustrated in FIG. 1A. RBMs may refer to bidirectional neural networks, where the neurons (also called units) are divided into two layers, a visible layer 104 and a hidden layer 102. The visible layer 104 ($v$) can describe the observed data. The hidden layer 102 ($h$) may include one or more set(s) of unobserved latent variables that capture the interactions between the visible units. RBMs may describe the joint probability distribution of v and h using an exponential form, $$p(v,h) = Z^{-1} e^{-E(v,h)}, \tag{1}$$

Here, E(v, h) may be called the energy function, and be used to train the RBM. Additionally or alternatively, $Z = \int dv dh e^{-E(v,h)}$ may be called the partition function, and used for normalization of the energy function. In many embodiments, processes can use the integral operator, $\int dx$, to denote both standard integration or a sum over all of the elements in a discrete set.

In a traditional RBM, both the visible 104 and hidden 102 units may be binary. Each can only take on the values 0 or 1. The energy function in accordance with numerous embodiments of the invention can then be written as, $$E(v, h) = -\sum_i a_i v_i - \sum_\mu b_\mu h_\mu - \sum_{i\mu} W_{i,\mu} v_i h_\mu \tag{2}$$

and/or, in vector notation, as $E(v,h) = -a^T v - b^T h - v^T W h$, wherein $a_i \in a$ and $b_i \in b$ are unconstrained, real-valued learnable parameters. In accordance with numerous embodiments of the invention, visible units 104 may interact with the hidden units 102 through the weights, W. However, in accordance with some embodiments, there may not be visible-visible and/or hidden-hidden interactions. Instead the layers 102, 104 can be restricted to interactions between layers.

A key feature of an RBM configured in accordance with certain embodiments may be the ease of computing conditional probabilities for the layers, $$p(v \mid h) = \prod_i \frac{e^{(a_i + \sum_\mu W_{i\mu} h_\mu) v_i}}{1 + e^{a_i + \sum_\mu W_{i\mu} h_\mu}} \tag{3}$$

-continued $$\text{and, } p(h \mid v) = \prod_\mu \frac{e^{(b_\mu + \sum_i W_{i\mu} v_i) h_\mu}}{1 + e^{b_\mu + \sum_i W_{i\mu} v_i}}. \tag{4}$$

Similarly, it can easy to compute the conditional moments, $$v_{p(v|h)} = \frac{1}{1 + e^{-(a + Wh)}} \tag{5}$$

$$\text{and, } h_{p(h|v)} = \frac{1}{1 + e^{-(b + W^T v)}}. \tag{6}$$

RBMs can be trained by maximizing a log-likelihood function $\mathcal{L} := \log p(v)_{data} = \log \int dh p(v, h)_{data}$. Here, $\cdot_{data}$ may denote an average over all of the observed samples. The derivative of the log-likelihood with respect to some parameter of the model $\theta$ is:

$$\frac{\partial \mathcal{L}}{\partial \theta} = \frac{\partial}{\partial \theta} \log \int dh p(v, h)_{data} = \tag{7}$$

$$\frac{\partial}{\partial \theta} \log \int dh e^{-E(v,h)}_{data} - \frac{\partial}{\partial \theta} \log Z = \frac{\int dh e^{-E(v,h)} (-\frac{\partial E}{\partial \theta})}{\int dh e^{-E(v,h)}}_{data} -$$

$$\frac{\int dv dh e^{-E(v,h)} (-\frac{\partial E}{\partial \theta})}{\int dv dh e^{-E(v,h)}} = \frac{\partial E}{\partial \theta}_{p(v,h)} - \frac{\partial E}{\partial \theta}_{p(h|v)data}$$

In the standard formulation of an RBM, there are three parameters a, b, and W. The derivatives are:

$$\frac{\partial \mathcal{L}}{\partial a} = v_{p(v,h)} - v_{data} \tag{8}$$

$$\frac{\partial \mathcal{L}}{\partial b} = h_{p(v,h)} - h_{p(h|v)data}$$

$$\frac{\partial \mathcal{L}}{\partial W} = vh^T_{p(v,h)} - vh^T_{p(h|v)data}$$

Computing expectations from the joint distribution is generally computationally intractable. Therefore, statistics from the joint distribution including but not limited to the derivatives may be estimated using random sampling processes such as Markov Chain Monte Carlo (MCMC) processes.

2. Conditional Restricted Boltzmann Machines (CRBMs)

In accordance with many embodiments of the invention, a Conditional RBM (CRBM) may refer to an RBM where some of the parameters are not free are instead parametrized functions of a conditioning random variable (i.e., may be predicted by an RV with significant levels of precision). As such, newly obtained (temporal) information may be added to CBRMs as delayed units on the visible layer.

Turning now to the drawings, a CRBM configured in accordance with a number of embodiments of the invention is illustrated in FIG. 1B. The example of FIG. 1B shows a conditional RBM with a visible layer 108, 110, 112, and a hidden layer 106. As is the case for a traditional RBM, the nodes (also referred to herein as "units") of the visible layer 108, 110, 112, may be connected to nodes of the hidden layer 106. In accordance with many embodiments of the invention, nodes of the hidden layer 106 (hidden units) may be used to create latent spaces to model the data distributions of interest. The visible layer, may refer to a composite layer comprised of several nodes (visible units) of various types (e.g., continuous, categorical, and/or binary).

In accordance with certain embodiments, a Conditional RBM (CRBM) can be defined using the energy function $$\mathcal{H}(v_{t+1}, v_t, h) = \mathcal{H}(v_{t+1}, h) + \mathcal{H}(v_t, h) + \sum_{\mu} b_{\mu}(h_{\mu}) \qquad (9)$$

where each component energy is of the same form as the RBM energy function above. Additionally or alternatively, within the energy function, v t may represent the visible units at time step t represented in vector form.

As a result, RBMs may be extended to include a notion of temporal history, in the form of CRBMs. In accordance with many embodiments of the invention, a single input vector may contain x features, which may be mapped to the visible random variables $v_t$ corresponding to the visible units 112 in the current time iteration (t). There are undirected connections between these visible units and the hidden units. Alone, these connections form an unaltered RBM for the input vector at time step t. However, the CRBM can also incorporate additional directed or undirected connections from the input vectors at the previous time steps (e.g., t–1). As a result, systems may define CRBMs as models encompassing RBMs whose probability distributions depend conditionally on the visible random variables (e.g., $v_{t-1}$ 110, $v_0$ 108) corresponding to the visible units of a number of previous time points. For CRBMs, the joint distribution of the (current) visible and hidden units 106 conditioned on the previous visible units 108, 110 can be reordered as:

$$\mathcal{H}(v_{t+1}, h \mid v_t) = \mathcal{H}(v_{t+1}, h) - \sum_{i\mu} W_{i\mu}^{(t)} a_i^{(t)}(v_{t,i}) b_{\mu}(h_{\mu}). \qquad (10)$$

3. Neural Conditional Restricted Boltzmann Machines (nCRBMs)

Systems and methods in accordance with many embodiments of the invention may be applied, through the conditional distributions including but not limited to Equation (1) to turning pre-existing point prediction models into conditional generative models. FIG. 1C illustrates the implementation of CRBMs (and RBMs) incorporating point prediction models in accordance with various embodiments of the invention. In particular, such cases may use the point prediction models 118 ($f_\theta(x)$) as CRBM components. In accordance with many embodiments of the invention, point prediction models may refer to various models capable of providing point estimates of outcomes based on input features, including but not limited to linear models, neural networks, decision trees, and/or other predictive model classifications. In using such point prediction models, systems may be applied to determining mathematical models of probability distribution (p(y|x)) for multivariate outcome vectors 122, 124, 126 ($y_i \in y$), conditioned on input features 114 (x), which may also be referred to as conditional generative models. In accordance with many embodiments of the invention, values in outcome vectors may be continuous, binary, ordinal, one-hot encoded categorical, and/or various other types of variables.

Additional CRBM components may include but are not limited to hidden layers 122 (e.g., h), weight matrices 116 (e.g., W), and precision matrices 120 (e.g., P). In accordance with a number of embodiments of the invention, weight matrices 116 and precision matrices 120 may, additionally or alternatively, be represented as functions. For example, P 120 may instead be a function of the input features 114 (P(x)). Additionally or alternatively, W 116 may instead be a function of the input features 114 (W(x)).

Systems in accordance with a number of embodiments of the invention may be configured to produce conditional generative models obtained from a combination of a probabilistic model (including but not limited to RBMs and/or CRBMs) and a point prediction model 118. The combination of probabilistic models and point prediction models 118 may, in this application, be referred to as "combinations", "conditional generative models" and/or "neural Conditional Restricted Boltzmann Machines" (nCRBMs) in this application. Nevertheless, in accordance with certain embodiments of the invention, prospective point prediction models are not limited to neural networks.

Figure 2:
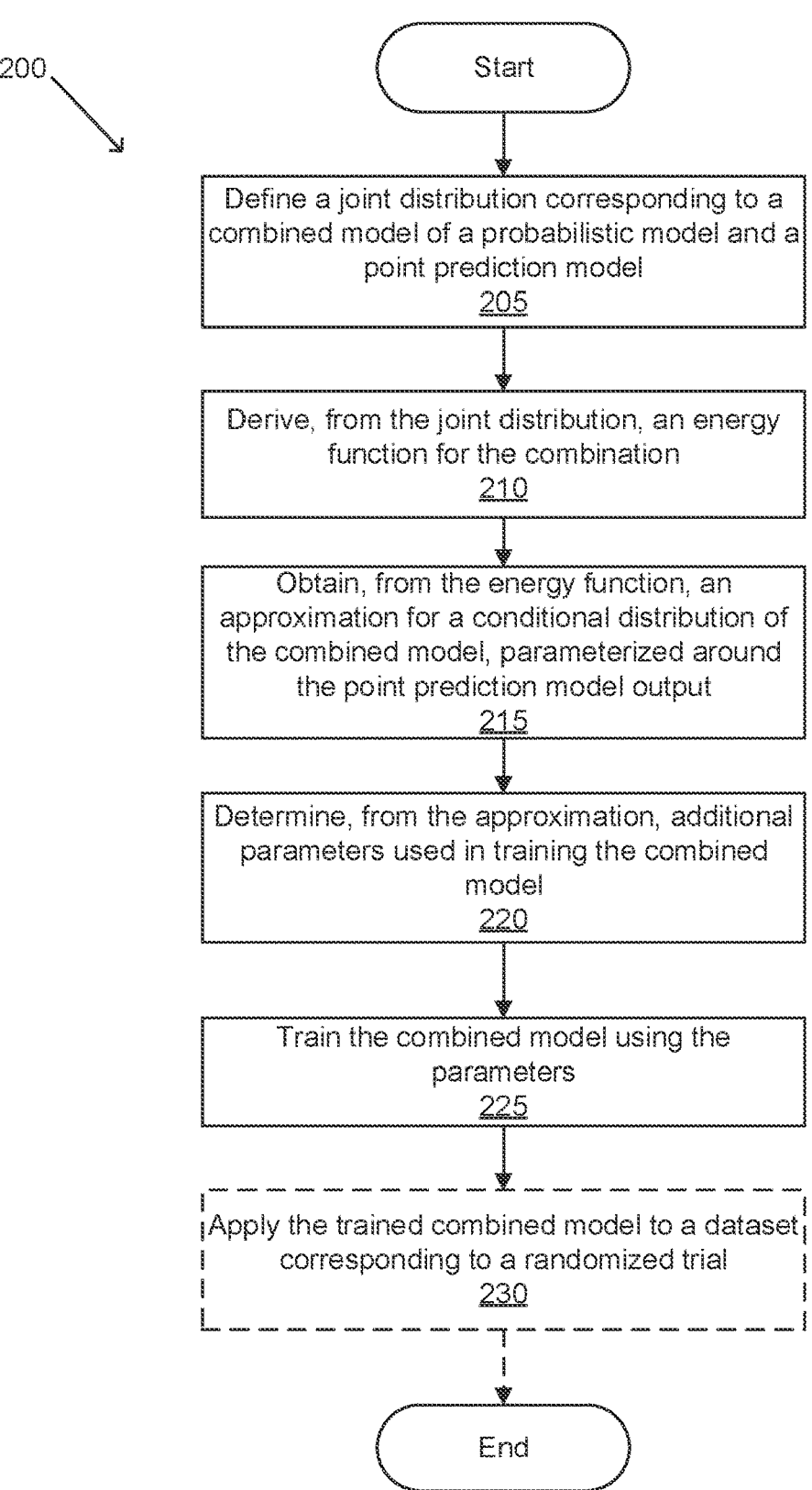
FIG. 2 conceptually illustrates a process for deriving and applying conditional generative models in accordance with many embodiments of the invention.

A process for deriving and applying conditional generative models, obtained from nCRBMs configured in accordance with many embodiments of the invention, is illustrated in FIG. 2. Process 200 defines (205) a joint distribution corresponding to a combination of a probabilistic model and a point prediction model. In accordance with many embodiments of the invention, the combination of the probabilistic model and the point prediction model may correspond to the nCRBM. As indicated above, probabilistic models may include but are not limited to CRBMs. In accordance with several embodiments of the invention, point prediction models may be configured to derive conditional means (E[y|x]) in terms of a function $f_\theta(x)$ parameterized by θ. In accordance with numerous embodiments of this invention, point predictions may be derived based on estimates including but not limited to the minimization of ordinary least squares (OLS) for y|x:

$$OLS(\theta) = E_{p_{data}(y,x)}[(y - f_\theta(x))^2] \qquad (11)$$

In accordance with some embodiments, when the probabilistic model is a CRBM, the joint distribution of the resulting nCRBM, with visible units y, hidden units h, and feature units x, may be represented as: $y_{t+\delta t}$.

$$p(y,h|x) = Z^{-1}(x)e^{-U(y,h|x)} \qquad (12)$$

where $Z(x) = \int dy \sum_H e^{U(y,h|x)}$ is the normalization constant.

Process 200 derives (210), from the joint distribution, an energy function for the conditional generative model. In accordance with many embodiments of the invention, process 200 may obtain the energy function for the conditional generative model (U(y|k)) from the energy function for the joint distribution. As such, the term U(y,h|x) may represent the energy function for the joint distribution and take the form:

$$U(y, h \mid x) = \frac{1}{2}(y - f_\theta(x))' P(y - f_\theta(x)) - (y - f_\theta(x))' W h \qquad (13A)$$

where P, the precision matrix, is a diagonal positive definite matrix and W is a weight matrix. In accordance with a few embodiments, the hidden units (h) may take forms including but not limited to Ising spins where $h_i = \pm 1$. When y is a continuous, real-valued vector, the energy function of y|x (i.e., the conditional generative model) can be derived by marginalizing and/or summing over the states of the hidden units (e.g., $p(y|x)=\Sigma_H p(y, h|x)$). In doing so, the resulting marginal energy function ($\mathcal{U}(y|x)$) may take the form:

$$\mathcal{U}(y \mid x) = \frac{1}{2}(y - f_\theta(x))'P(y - f_\theta(x)) - \log Tr_h e^{(y-f_\theta(x))'Wh} = \tag{13B}$$

$$\frac{1}{2}(y - f_\theta(x))'P(y - f_\theta(x)) - \sum_j \log\cosh\left(\sum_i W_{ij}(y - f_\theta(x))_i\right) =$$

$$\frac{1}{2}(y - f_\theta(x))'P(y - f_\theta(x)) - \sum_j \log\cosh\left(w_{j'}(y - f_\theta(x))\right) =$$

$$\frac{1}{2}(y - f_\theta(x))'P(y - f_\theta(x)) - 1'\log\cosh(W'(y - f_\theta(x))).$$

Additionally or alternatively, P may instead be a function of the input features (x) parameterized by parameter $\phi(P_\phi(x))$. Additionally or alternatively, W may instead be a function of the input features (x) parameterized by parameter $\psi(W_\psi(x))$. In such cases:

$$\mathcal{U}(y, h \mid x) = \frac{1}{2}(y - f_\theta(x))'P_\phi(x)(y - f_\theta(x)) - (y - f_\theta(x))'W_\psi(x)h. \tag{13C}$$

$$\mathcal{U}(y \mid x) = \tag{13D}$$
$$\frac{1}{2}(y - f_\theta(x))'P_\phi(x)(y - f_\theta(x)) - 1'\log\cosh(W'_\psi(x)(y - f_\theta(x))).$$

Process 200 obtains (215), from the energy function (for the conditional generative model) and the point prediction model, an approximation for a conditional distribution of the conditional generative model parameterized around the point prediction model output. In accordance with many embodiments of the invention, approximations may include but are not limited to Laplace approximations. For an example with a continuous y, taking the derivatives of the energy function with respect to y:

$$\frac{\partial \mathcal{U}}{\partial y} = P(y - f_\theta(x)) - W\tanh(W'(y - f_\theta(x))), \tag{14A}$$

$$\frac{\partial^2 \mathcal{U}}{\partial y^2} = P - W\operatorname{diag}\left(1 - \tanh^2(W'(y - f_\theta(x)))\right)W'. \tag{15A}$$

and evaluating the derivatives at $y=f_\theta(x)$ may yield:

$$\frac{\partial \mathcal{U}}{\partial y}\Big|_{y=f_\theta(x)} = 0, \tag{14B}$$

$$\frac{\partial^2 \mathcal{U}}{\partial y^2}\Big|_{y=f_\theta(x)} = P - WW'. \tag{15B}$$

This method may be used to conclude that $y=f_\theta(x)$ is a local minimum of the energy function when y is continuous and real-valued and P–WW' is positive definite. As a result, the Laplace approximation for y conditioned on x may take the form:

$$y|x \sim \mathcal{N}(f_\theta(x), (P-WW')^{-1}). \tag{16}$$

where P is a precision matrix and W is a weight matrix. As described above, both precision matrices (e.g., P) and weight matrices (e.g., W) may be represented as functions (e.g., $P_\phi(x), W_\psi(x)$). In accordance with certain embodiments of the invention, $y=f_\theta(x)$ may be a local minimum of the energy function when $P_\phi(x)-W_\psi(x)W_\psi(x)'$ is positive definite.

In accordance with a number of embodiments of the invention, nCRBMs may normalize values in the weight matrix. For example, when W may be normalized by values including but not limited to $$(n_y)^{-\frac{1}{2}},$$

wherein $n_y$ may represent the number of participants in a particular arm of a clinical trial for example. This normalization may be performed in order to better condition the matrix P–WW' (where P may be $P_\phi(x)$, W may be $W_\psi(x)$, and/or $(P-WW')^{-1}$ may be a covariance matrix representing the covariance of the residual noise process). Systems configured in accordance with multiple embodiments of the invention may add additional loss during training including but not limited to logarithms of the determinant of the P–WW', logarithms of conditions numbers, and/or other constraints on positive definiteness.

Process 200 determines (220), from the approximation, terms used in training the combination (e.g., the nCRBM) to operate as a conditional generative model. In accordance with some embodiments, nCRBMs may be trained by minimizing loss functions that may include but are not limited to negative log-likelihood functions. In accordance with many embodiments of the invention, the negative log-likelihood function may take the form:

$$\mathcal{L} = -E_{P_{data}(x)}\left[E_{P_{data}(y|x)}\left[\log Z(x)^{-1}\sum_H e^{-U(y,h|x)}\right]\right], \tag{17}$$

$$= E_{P_{data}(x)}\left[\log Z(x) - E_{P_{data}(y|x)}\left[\log \sum_H e^{-U(y,h|x)}\right]\right].$$

The training of nCRBMs, configured in accordance with certain embodiments of the invention, is expounded upon below.

Process 200 trains (225) the conditional generative model. In many embodiments, energy-based models can be trained using gradient descent. Gradients used in training the conditional generative model may be obtained from various derivatives of the loss function. In minimizing the negative log-likelihood function, the derivative of Equation (17) with respect to a particular parameter $\phi$ may take the form:

$$\frac{\partial \mathcal{L}}{\partial \phi} = E_{P_{data}(x)}\left[\log Z(x) - E_{P_{data}(y|x)}\left[\log Tr_h e^{-U(y,h|x)}\right]\right] = \tag{18}$$

$$E_{P_{data}(x)}\left[E_{p(y,h|x)}[-\partial_\phi U] - E_{P_{data}(y|x)}[E_{p(h|x,y)}[-\partial_\phi U]]\right] =$$

$$E_{P_{data}(x)}\left[E_{P_{data}(y|x)}[E_{p(h|x,y)}[\partial_\phi U]] - E_{p(y|x)}[E_{p(h|x,y)}[\partial_\phi U]]\cdot\right]$$

which may be used to minimize the loss function and thereby optimize the conditional generative model. In training the conditional generative model, process 200 may need to determine the terms that optimize Equation (18). This may be done using information including but not limited to data from historical datasets. In accordance with certain embodiments of the invention, expected values for $p(y|x)$ may be obtained and/or refined using obtained Monte Carlo samples. Additionally or alternatively, estimates for $p(h|x, y)$ can be obtained from integrating $h*p(h|x, y)$ over h, using Equations (12) and (13A). The result may be the following:

$$E_{p(h|x,y)}[h]=\tan h(W'(y-f_\theta(x))). \tag{19}$$

In doing so, process 200 may derive values for P and W in order to further improve the approximation of the conditional distribution p(y|x). As the precision matrix, P may be diagonal and positive definite. As such, systems in accordance with some embodiments may define P in terms of a vector b, a learned parameter, using P=diag($e^b$). In such a case, the gradients for vectors b and W may take the form:

$$\frac{\partial \mathcal{L}}{\partial b} = \frac{1}{2} e^b \odot \tag{20A}$$

$$\left(E_{P_{data}(x)}\left[E_{P_{data}(y|x)}\left[(y-f_\theta(x))^2\right]\right] - E_{P_{data}(x)}\left[E_{p(y|x)}\left[(y-f_\theta(x))^2\right]\right]\right),$$

$$\frac{\partial \mathcal{L}}{\partial W} = E_{P_{data}(x)}\left[E_{P_{data}(y|x)}\left[-(y-f_\theta(x))\tanh\left((y-f_\theta(x))'W\right)\right]\right] - \tag{21A}$$

$$E_{P_{data}(x)}\left[E_{p(y|x)}\left[-(y-f_\theta(x))\tanh\left((y-f_\theta(x))'W\right)\right]\right]$$

and be used to train the conditional generative model accordingly.

Systems and methods configured in accordance with various embodiments, may facilitate the training of point prediction components and the RBM component of an nCRBM simultaneously (which may be referred to as "end-to-end training"). When point prediction models $f_\theta(x)$ are differentiable with respect to the parameters θ, the above gradient formulas may take the forms:

$$\frac{\partial \mathcal{L}}{\partial b} = \frac{1}{2} e^b \odot \tag{20B}$$

$$\left(E_{P_{data}(x)}\left[E_{P_{data}(y|x)}\left[(y-f_\theta(x))^2\right]\right] - E_{P_{data}(x)}\left[E_{p(y|x)}\left[(y-f_\theta(x))^2\right]\right]\right),$$

$$\frac{\partial \mathcal{L}}{\partial W} = E_{P_{data}(x)}\left[E_{P_{data}(y|x)}\left[-(y-f_\theta(x))\tanh\left((y-f_\theta(x))'W\right)\right]\right] - \tag{21B}$$

$$E_{P_{data}(x)}\left[E_{p(y|x)}\left[-(y-f_\theta(x))\tanh\left((y-f_\theta(x))'W\right)\right]\right],$$

$$\frac{\partial \mathcal{L}}{\partial \theta} = E_{P_{data}(x)}\left[E_{P_{data}(y|x)}\left[-\frac{\partial f_\theta'(x)}{\partial \theta}\left(e^b \odot (y-f_\theta(x)) - \right.\right.\right. \tag{22}$$

$$\left.\left.\left. W\tanh\left(W'(y-f_\theta(x))\right)\right)\right]\right] - E_{P_{data}(x)}\left[E_{p(y|x)}\right.$$

$$\left.\left[-\frac{\partial f_\theta'(x)}{\partial \theta}\left(e^b \odot (y-f_\theta(x)) - W\tanh\left(W'(y-f_\theta(x))\right)\right)\right]\right]$$

allowing all the parameters of the conditional generative model to be learned via stochastic gradient descent.

In accordance with numerous embodiments, as mentioned above, P and W may operate as parameters that depend on x. As such, P(x) and W(x) may take the form of parameterized functions of the features x. Additionally or alternatively, process 200 may apply Equation 7 and/or Equation 5 to compute the gradients with respect to the parameters for training. In doing so, process 200 may define the general energy function, $$\mathcal{U}(y|x) = \frac{1}{2}(y-f_\theta(x))'P_\phi(x)(y-f_\theta(x)) - 1'\log\cosh\left(W_\psi'(x)(y-f_\theta(x))\right), \tag{23}$$

and use automatic differentiation to compute the gradients with respect to the parameters θ, φ, and ψ.

Process 200 may, in certain cases, apply (230) the trained conditional generative model to a dataset corresponding to a randomized trial. In accordance with numerous embodiments, y may correspond to certain randomized trial treatments, while x corresponds to pre-treatment covariates. In accordance with various embodiments, averages from the model conditional distribution can be estimated using Monte Carlo samples from the conditional distribution. As such, any Monte Carlo algorithm can be used for this. Additionally or alternatively, sampling methods including but not limited to Gibbs sampling, Persistent Contrastive Divergence sampling, and Gibbs-Langevin sampling may be applied to obtain these averages.

Systems and methods in accordance with many embodiments of the invention may be used to train nCRBMs. In particular, systems may use negative log-likelihood functions to train nCRBMs.

$$\mathcal{L}(\theta,\phi,\psi)=-E_{data}[\log p(y|x)], \tag{24}$$

based on the assumptions that:

$$p(y|x)=Z^{-1}(x)e^{-U(y|x)} \tag{25A}$$

and $$Z(x)=\int dy\Sigma_H e^{-U(y|x)}. \tag{25B}$$

In accordance with several embodiments of the invention, based on the above loss function, gradients may be derived according to particular model parameters (e.g., θ,φ,ψ) in the following form:

$$\frac{\partial \mathcal{L}}{\partial \theta} = -\frac{\partial}{\partial \theta} E_{data}[\log p(y|x)] = E_{data}\left[\frac{\partial}{\partial \theta}U(y|x)\right] + \tag{26}$$

$$E_{data}\left[\frac{\partial}{\partial \theta}\log \mathcal{Z}(x)\right] = E_{data}\left[\frac{\partial}{\partial \theta}U(y|x)\right] + E_{data}\left[\frac{\int dy \frac{\partial}{\partial \theta} e^{-U(y|x)}}{\int dy e^{-U(y|x)}}\right] =$$

$$E_{data}\left[\frac{\partial}{\partial \theta}U(y|x)\right] - E_{data}\left[E_{p(y|x)}\left[\frac{\partial}{\partial \theta}U(y|x)\right]\right]$$

where the first term $$E_{data}\left[\frac{\partial}{\partial \theta}U(y|x)\right]$$

(herein "the positive phase") may be obtained by taking the gradient of the energy function and averaging over observed (x, y) values. The positive phase integral may be comparatively easy to estimate using seeded Markov Chain Monte Carlo samples from the data distribution. Additionally or alternatively, the second term $$E_{data}\left[E_{p(y|x)}\left[\frac{\partial}{\partial \theta}U(y|x)\right]\right]$$

may be obtained through deriving gradients of the energy function and averaging that value over observed x values and/or generated y|x values.

In accordance with certain embodiments of the invention, backpropagation may be used to derive gradients in situations where $P_\phi(x)$,$W_\psi(x)$, and $f_\theta(x)$ are differentiable functions of φ,ψ and θ, respectively. In accordance with various embodiments of the invention, values for, $P_\phi(x)$, may be configured to remain non-negative through reparameterizations to learn $\log(P_\phi(x))$ in place of $P_\phi(x)$.

Systems configured in accordance with some embodiments of the invention may apply penalties including but not limited to L2 penalties to functions (e.g., $f_\theta(x)$, $P_\phi(x)$, and $W_\psi(x)$). In accordance with certain embodiments, systems may set the penalty on $W_\psi(x)$ to be larger than $f_\theta(x)$ and $P_\phi(x)$. For example, L2 penalties of 1.0 on $W_\psi(x)$ and 0.5 on $f_\theta(x)$ and $P_\phi(x)$ may be utilized in practice across a wide variety of problems. Implementation of such configurations are referenced in disclosure "Neural Boltzmann Machines" by Alex Lang et al., incorporated by reference in its entirety.

Systems and methods configured in accordance with a number of embodiments of the invention, may be trained in order to update model parameters. Training may involve sampling minibatches of data (e.g., $(x_i, y_i)$). The obtained samples may be used to perform initial backward passes to obtain values for $U(y|x)$ from using at least one of Equations (13B) and (13D). Additionally, k-steps of block Gibbs sampling may be used to generate $\tilde{y}_i$ conditioned on $x_i$. When these values are obtained, additional backward passes may be used to obtain values for $U(y|x)$, again from using at least one of Equations (13B) and (13D). The first term in the gradient $$\left( E_{data}\left[\frac{\partial}{\partial\theta} U(y|x)\right] \right)$$

may rye estimated by performing the initial backward passes. Additionally or alternatively, the second term in the gradient $$\left( E_{data}\left[ E_{p(y|x)}\left[\frac{\partial}{\partial\theta} U(y|x)\right]\right] \right)$$

may be estimated by sampling the aforementioned values for $\tilde{y}_i$ conditioned on $x_i$ and using those samples to estimate the integrals.

Figure 3:
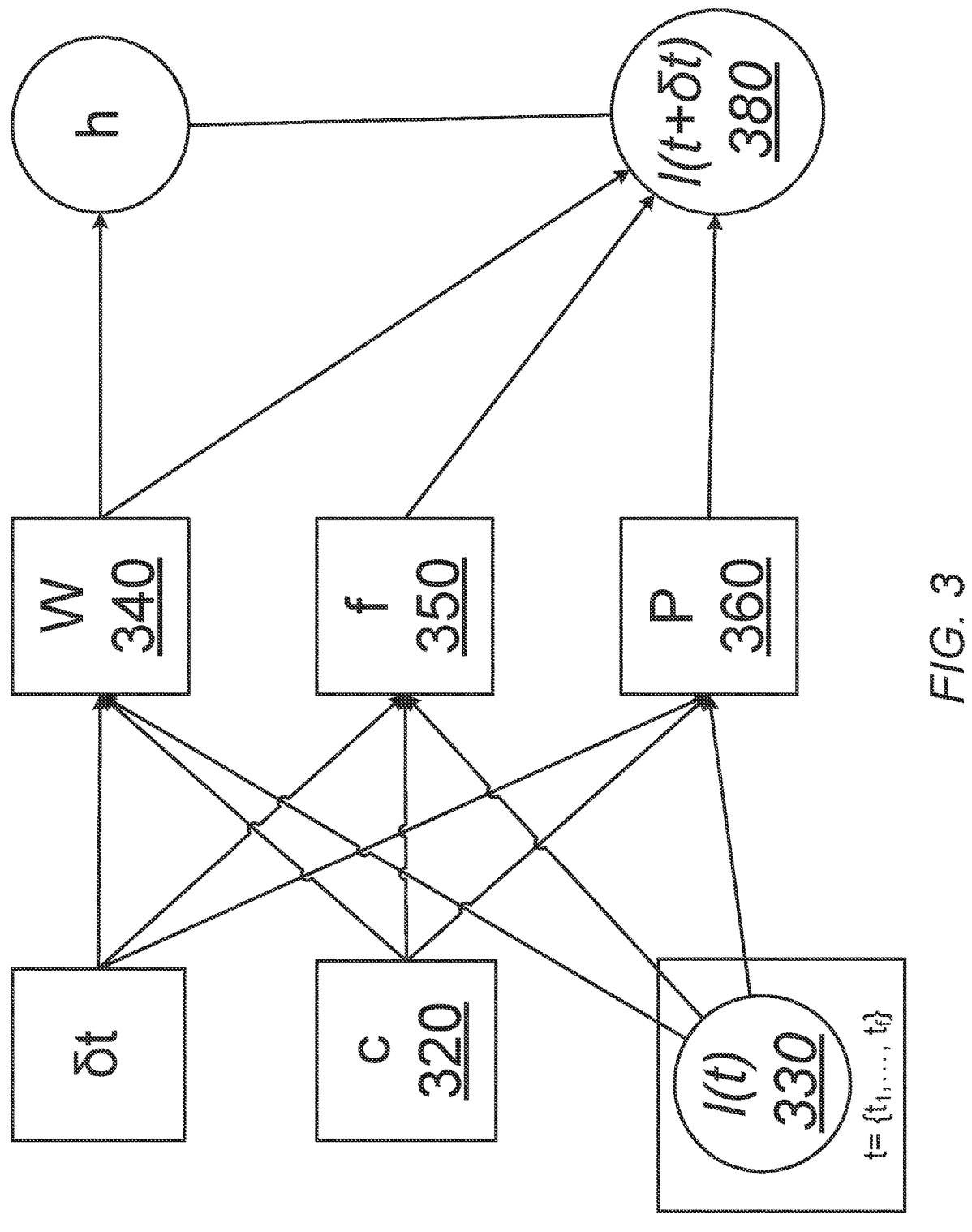
FIG. 3 illustrates the application of Neural Conditional Restricted Boltzmann Machines, configured in accordance with multiple embodiments of the invention, to time-series.

FIG. 3 illustrates the application of nCRBMs configured in accordance with many embodiments of the invention, to learning conditional generative models of time-series. Many problems (e.g., modeling patient trajectories) addressed in accordance with some embodiments of the invention may utilize the capacity to generate time-series. In doing so, they may generate a sequence of states $$L_{t_0:t_f} = \{l(t)\}_{t=t_0}^{t=t_f}$$

330. In one example, $$L_{t_0:t_f} = \{l(t)\}_{t=t_0}^{t=t_f}$$

may denote a realization of a stochastic process 330 from time $t_0$ to time $t_f$. Additionally or alternatively, c may denote a vector of time-independent context variables 320. In the example, the conditional generative model for the time-series can be trained by learning the transition density $p(l(t+\delta t)|L_{t_0:t}, c, \delta t)$. In accordance with some embodiments of the invention, transition density may be represented with nCRBMs.

In accordance with many embodiments of the invention, $f_\theta(L_{t_0:t}, c, t, \delta t)$ may represent a point predictor 350 for $l(t+\delta t)$ 380. As such, point predictors may take the form of deterministic functions that predict the states 380 of stochastic processes at time $t+\delta t$ from the entire history up until time $t_f$. As suggested above, P 360 and/or W 340 may be represented as parameterized functions. In some instances, systems configured in accordance with various embodiments may define $P_\phi(L_{t_0:t}, c, t, \delta t)$ and $W_\psi(L_{t_0:t}, c, t, \delta t)$ as parameterized functions of the entire temporal history. As such, $f_\theta$, $P_\phi$ and/or $W_\psi$ may input values including but not limited to $$L_{t_0:t_f} = \{l(t)\}_{t=t_0}^{t=t_f}, c, t = \{t_1, \dots, t_f\},$$

and/or $\delta t$. Additionally or alternatively, simple approximations may assume that the covariance matrix approximately scales like a diffusion, wherein $(P-WW')^{-1}\sim\delta t$. In such an example, systems may determine that $P\sim1/\delta t$ and $W\sim1/\sqrt{\delta t}$. Other approximations used may include but are not limited to general approximations. Regardless, when diffusion approximations are used the resulting joint energy function may take the form:

$$U(l(t+\delta t), h|L_{t_0:t}, c) = \tag{27A}$$

$$\frac{1}{2}(l(t+\delta t) - f_\theta(L_{t_0:t}, c, t, \delta t))'\frac{P}{\delta t}(l(t+\delta t) - f_\theta(L_{t_0:t}, c, t, \delta t)) -$$

$$(l(t+\delta t) - f_\theta(L_{t_0:t}, c, t, \delta t))'\frac{W}{\sqrt{dt}} h,$$

which corresponds to the marginal energy function:

$$U(l(t+\delta t)|L_{t_0:t}, c) = \tag{27B}$$

$$\frac{1}{2}(l(t+\delta t) - f_\theta(L_{t_0:t}, c, t, \delta t))'\frac{P}{\delta t}(l(t+\delta t) - f_\theta(L_{t_0:t}, c, t, \delta t)) -$$

$$1'\log\cosh\left(\frac{W'}{\sqrt{dt}}(l(t+\delta t) - f_\theta(L_{t_0:t}, c, t, \delta t))\right).$$

With this energy function derived, systems may apply Equation 7 to compute the gradients with respect to the parameters for training.

While specific modules for modeling complex probability distributions are described above, any of a variety of processes can be utilized to generate models as appropriate to the requirements of specific applications. In certain embodiments, steps may be executed or performed in any order or sequence not limited to the order and sequence shown and described. In a number of embodiments, some of the above steps may be executed or performed substantially simultaneously where appropriate or in parallel to reduce latency and processing times. In some embodiments, one or more of the above steps may be omitted.

System for Modeling Probability Distributions

Figure 4:
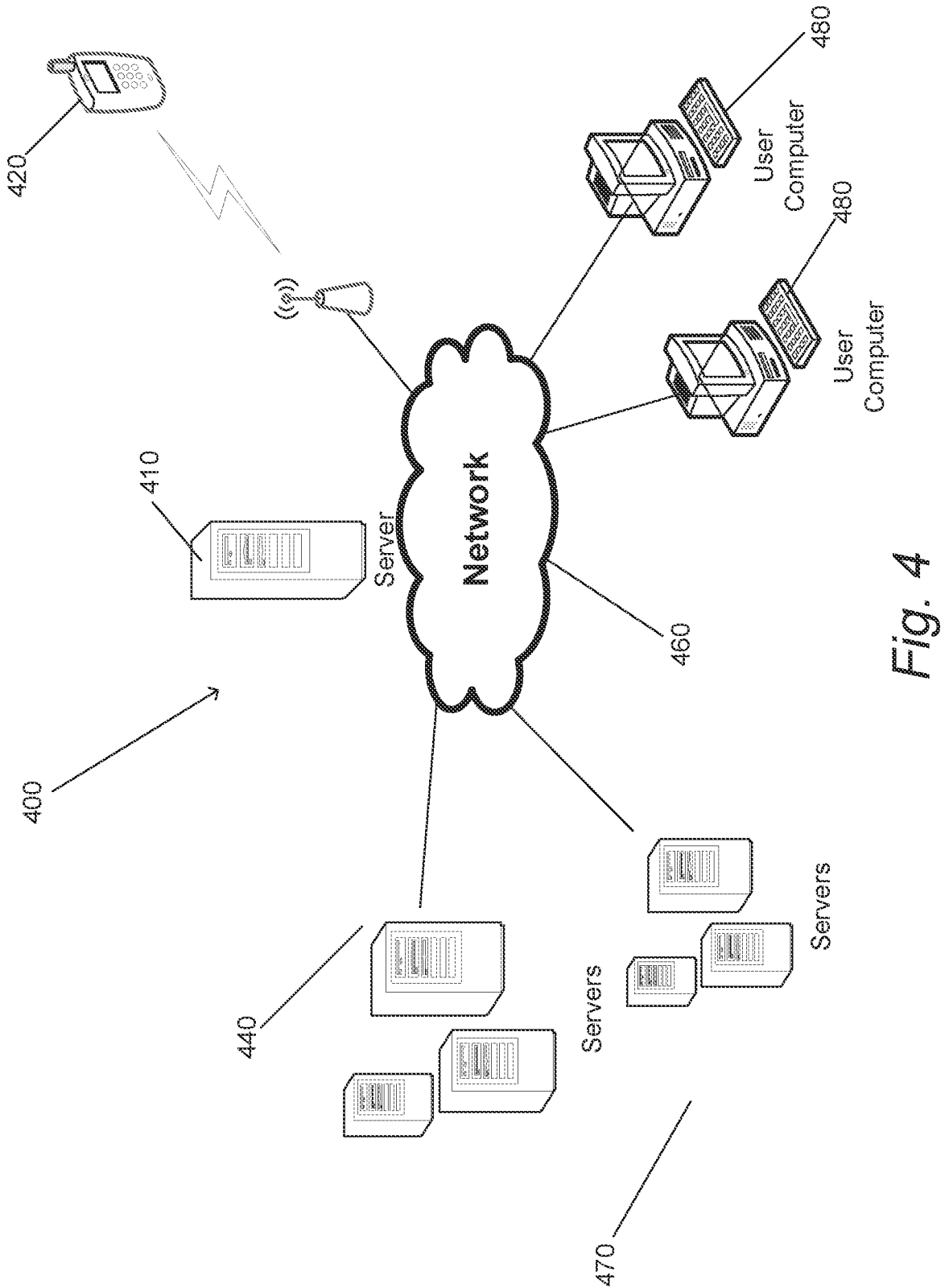
FIG. 4 illustrates a system that provides for the gathering and distribution of data for modeling probability distributions in accordance with numerous embodiments of the invention.

A system that provides for the gathering and distribution of data for modeling probability distributions in accordance with some embodiments of the invention is shown in FIG. 4. Network 400 includes a communications network 460. The communications network 460 is a network such as the Internet that allows devices connected to the network 460 to communicate with other connected devices. Server systems 410, 440, and 470 are connected to the network 460. Each of the server systems 410, 440, and 470 is a group of one or more servers communicatively connected to one another via internal networks that execute processes that provide cloud services to users over the network 460. For purposes of this discussion, cloud services are one or more applications that are executed by one or more server systems to provide data and/or executable applications to devices over a network. The server systems 410, 440, and 470 are shown each having three servers in the internal network. However, the server systems 410, 440 and 470 may include any number of servers and any additional number of server systems may be connected to the network 460 to provide cloud services. In accordance with various embodiments of this invention, a network that uses systems and methods that model complex probability distributions in accordance with an embodiment of the invention may be provided by a process (or a set of processes) being executed on a single server system and/or a group of server systems communicating over network 460.

Users may use personal devices 480 and 420 that connect to the network 460 to perform processes for providing and/or interacting with a network that uses systems and methods that model complex probability distributions in accordance with various embodiments of the invention. In the shown embodiment, the personal devices 480 are shown as desktop computers that are connected via a conventional "wired" connection to the network 460. However, the personal device 480 may be a desktop computer, a laptop computer, a smart television, an entertainment gaming console, or any other device that connects to the network 460 via a "wired" connection. The mobile device 420 connects to network 460 using a wireless connection. A wireless connection is a connection that uses Radio Frequency (RF) signals, Infrared signals, or any other form of wireless signaling to connect to the network 460. In FIG. 4, the mobile device 420 is a mobile telephone. However, mobile device 420 may be a mobile phone, Personal Digital Assistant (PDA), a tablet, a smartphone, or any other type of device that connects to network 460 via wireless connection without departing from this invention.

Figure 5A:
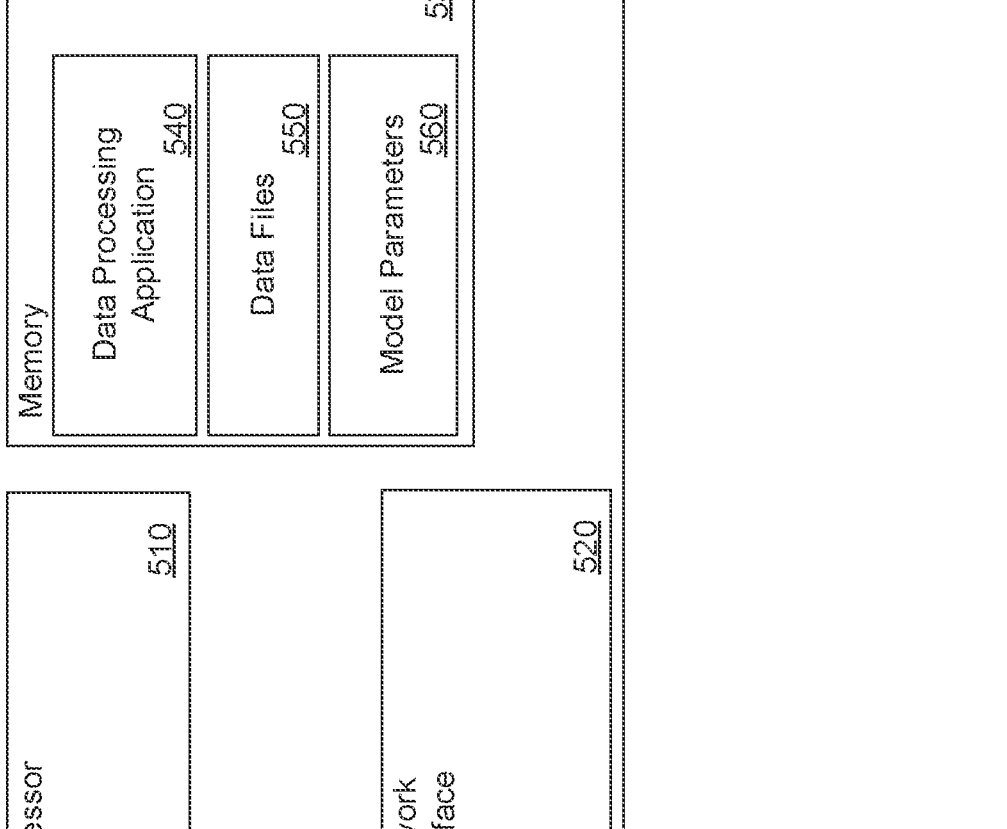
FIGS. 5A-5B illustrates data processing configurations constructed in accordance with various embodiments of the invention.

A data processing element for training and utilizing a stochastic model in accordance with a number of embodiments is illustrated in FIG. 5A. In various embodiments, data processing element 500 is one or more of a server system and/or personal devices within a networked system similar to the system described with reference to FIG. 4. Data processing element 500 includes a processor (or set of processors) 510, network interface 520, and memory 530. The network interface 520 is capable of sending and receiving data across a network over a network connection. In a number of embodiments, the network interface 520 is in communication with the memory 530. In several embodiments, memory 530 is any form of storage configured to store a variety of data, including, but not limited to, a data processing application 540, data files 550, and model parameters 560. Data processing application 540 in accordance with some embodiments of the invention directs the processor 510 to perform a variety of processes, such as (but not limited to) using data from data files 550 to update model parameters 560 in order to model complex probability distributions.

Figure 5B:
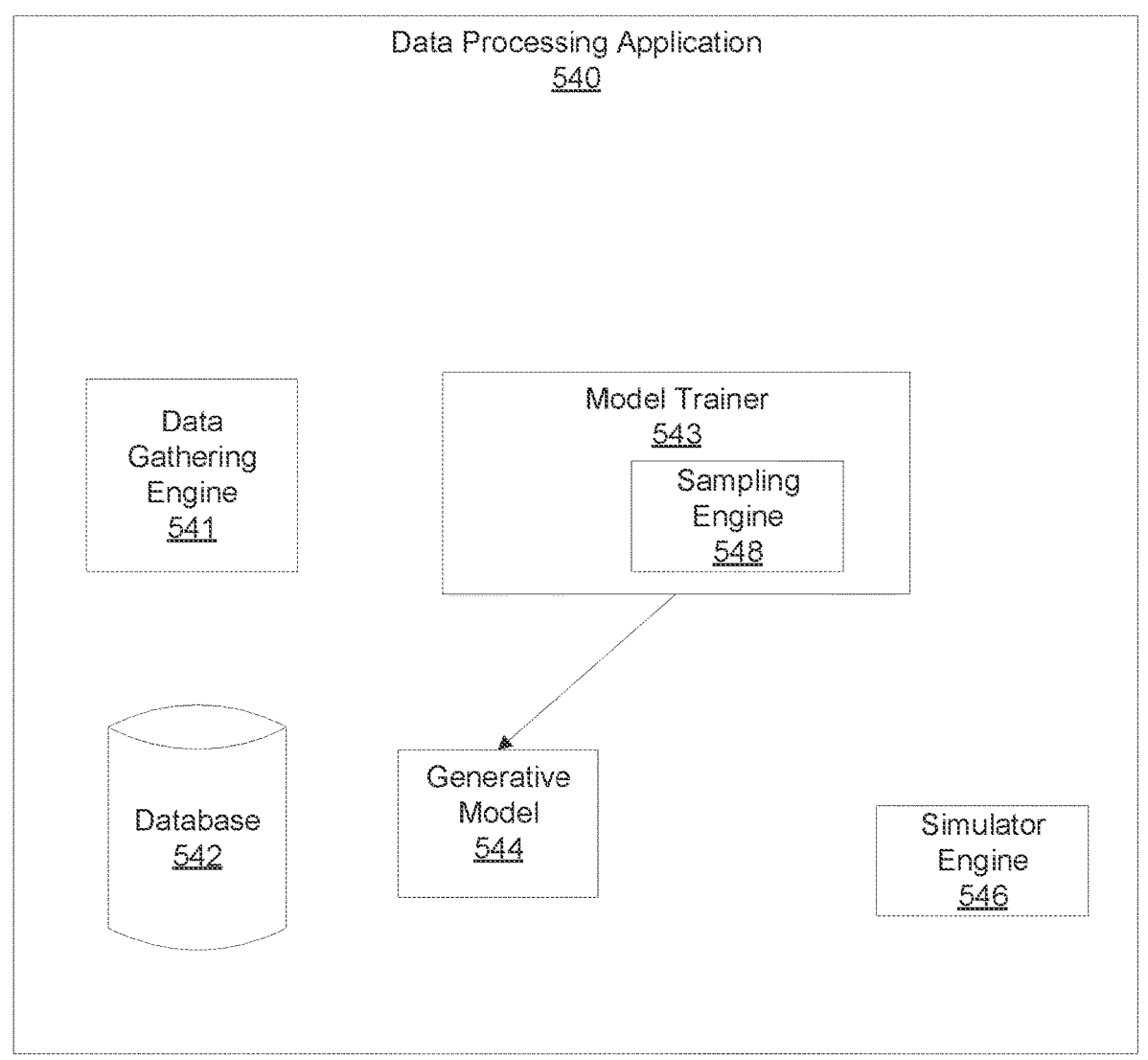

A data processing application in accordance with a number of embodiments of the invention is illustrated in FIG. 5B. In this example, data processing application 540 includes a data gathering engine 541, database 542, a model trainer 543, a generative model 544, a discriminator model 545, and a simulator engine 546. Model trainer 543 includes a schema processor 547 and a sampling engine 548. Data processing applications in accordance with many embodiments of the invention process data to train stochastic models that can be used to model complex probability distributions.

Databases in accordance with various embodiments of the invention store data for use by data processing applications, including (but not limited to) input data, pre-processed data, model parameters, schemas, output data, and simulated data. In some embodiments, databases are located on separate machines (e.g., in cloud storage, server farms, networked databases, etc.) from a data processing application.

Model trainers in accordance with a number of embodiments of the invention are used to train generative and/or discriminator models. In many embodiments, model trainers utilize schema processors to build the generator and/or discriminator models based on schemas that are defined for the various data available to the system. Schema processors in accordance with some embodiments of the invention build composite layers for a generative model (e.g., restricted Boltzmann machine) that are made up of several different layers for handling different types of data in different ways. In some embodiments, model trainers train the generative and discriminator models by optimizing a compound objective function based on log-likelihood and adversarial objectives. Training generative models in accordance with certain embodiments of the invention may utilize sampling engines to draw samples from the models to measure the probability distributions of the data and/or the models. Various methods for sampling from such models to train and/or draw generated samples from a model are described in greater detail below.

In many embodiments, generative models are trained to model complex probability distributions, which can be used to generate predictions/simulations of various probability distributions. Discriminator models discriminate between data-based samples and model-generated samples based on the visible and/or hidden states.

Simulator engines in accordance with several embodiments of the invention are used to generate simulations of complex probability distributions. In some embodiments, simulator engines are used to simulate patient populations, disease progressions, and/or predicted responses to various treatments. Simulator engines in accordance with several embodiments of the invention use a sampling engine for drawing samples from the generative models that simulate the probability distribution of the data.

As described above, as a part of the data-gathering process, the data in accordance with several embodiments of the invention is pre-processed in order to simplify the data. Unlike other pre-processing which is often highly manual and specific to the data, this can be performed automatically based on the type of data, without additional input from another person.

Applications and methods in accordance with various embodiments of the invention are not limited to modeling complex probability distributions or implementing generative models. Accordingly, it should be appreciated that the data collection capabilities of any system, application, and/or element described herein can also be implemented outside the context of generative modelling. Various systems and methods for configuring probability distributions in accordance with numerous embodiments of the invention are discussed further below.

Although specific methods of producing conditional generative models are discussed above, many different methods of model production can be implemented in accordance with many different embodiments of the invention. It is, therefore, to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

Systems and techniques for producing conditional generative models, are not limited to use for randomized controlled trials. Accordingly, it should be appreciated that applications described herein can be implemented outside the context of generative model architecture and in contexts unrelated to RCTs. Moreover, any of the systems and methods described herein with reference to FIGS. 1A-5B can be utilized within any of the generative models described above.

What is claimed is:

1. A method for training a conditional generative model, the method comprising:

defining a joint distribution, wherein:
    the joint distribution corresponds to a combination model comprising a probabilistic model and a point prediction model; and
    the point prediction model is configured to obtain a measurement of regression accuracy;
deriving an energy function for the joint distribution;
obtaining, from the energy function for the joint distribution, an approximation for a conditional distribution, wherein an output of the point prediction model is configured to derive a conditional mean parameter for the approximation;
determining, from a loss function corresponding to the approximation for the conditional distribution, at least one training parameter;
training the combination model to operate as a conditional generative model that follows the conditional distribution, wherein training the combination model comprises:
    defining a plurality of schema, according to a plurality of data types associated with a training dataset;
    configuring, using a schema processor and based on the plurality of schema, at least one visible layer of the probabilistic model to be a composite layer, wherein each constituent layer of the composite layer corresponds to at least one individual data type of the plurality of data types;
    inputting, into the at least one visible layer, the training dataset; and
    implementing a gradient descent using:
        at least one derivative of the at least one training parameter; and
        observed sample values output by the at least one visible layer of the probabilistic model;
inputting a trial dataset corresponding to a randomized trial into the trained combination model to output a multivariate output vector comprising an estimated outcome, wherein the estimated outcome:
    is based on a plurality of pre-trial covariates, included in the trial dataset; and
    comprises:
        a point estimate for at least one characteristic in the estimated outcome; and
        an outcome distribution, representing variability in the point estimate.

2. The method of claim 1, wherein the probabilistic model is a conditional restricted Boltzmann machine (CRBM).

3. The method of claim 2, wherein applying the trained probabilistic model to the trial dataset corresponding to the randomized trial comprises using the CRBM to generate a set of samples of a target population.

4. The method of claim 3, wherein the joint distribution is represented as:

$$p(y,h|x)=Z^{-1}(x)e^{-U(y,h|x)}$$

wherein:
    y represents visible units of the CRBM, h represents hidden units of the CRBM, x represents feature units of the CRBM, Z(x) represents a normalization constant, and U(y, h|x) is the energy function; and
    the normalization constant is represented as:

$$Z(x)=\int dy \Sigma_H e^{-U(y,h|x)}$$

5. The method of claim 1, wherein a gradient that is used in the gradient descent is obtained from at least one of:
    backpropagation; or
    automatic differentiation.

6. The method of claim 2, wherein deriving, from the joint distribution, the energy function for the probabilistic model comprises summing over states of hidden units of the CRBM.

7. The method of claim 1, wherein the measurement of regression accuracy is a minimum mean squared error prediction.

8. The method of claim 1, wherein the approximation is a Laplace approximation.

9. The method of claim 1,
    wherein a mode of the conditional distribution is identified by the point prediction model, and
    wherein the point prediction model comprises at least one selected from the group consisting of a linear model, a neural network, a decision tree, and a differential model.

10. The method of claim 1, wherein the loss function is a negative log-likelihood function.

11. A non-transitory computer-readable medium, for training a conditional generative model, comprising program instructions that are executable by one or more processors to perform a process that comprises:

defining a joint distribution, wherein:
    the joint distribution corresponds to a combination model comprising a probabilistic model and a point prediction model; and
    the point prediction model is configured to obtain a measurement of regression accuracy;
deriving an energy function for the joint distribution;
obtaining, from the energy function for the joint distribution, an approximation for a conditional distribution, wherein an output of the point prediction model is configured to derive a conditional mean parameter for the approximation;
determining, from a loss function corresponding to the approximation for the conditional distribution, at least one training parameter;
training the combination model to operate as a conditional generative model that follows the conditional distribution, wherein training the combination model comprises:
    defining a plurality of schema, according to a plurality of data types associated with a training dataset;
    configuring, using a schema processor and based on the plurality of schema, at least one visible layer of the probabilistic model to be a composite layer, wherein each constituent layer of the composite layer corresponds to at least one individual data type of the plurality of data types;
    inputting, into the at least one visible layer, the training dataset; and implementing a gradient descent using:

at least one derivative of the at least one training parameter; and observed sample values output by the at least one visible layer of the probabilistic model;

inputting a trial dataset corresponding to a randomized trial into the trained combination model to output a multivariate output vector comprising an estimated outcome, wherein the estimated outcome:

is based on a plurality of pre-trial covariates, included in the trial dataset; and comprises:

a point estimate for at least one characteristic in the estimated outcome; and an outcome distribution, representing variability in the point estimate.

12. The non-transitory computer-readable medium of claim 11, wherein the probabilistic model is a conditional restricted Boltzmann machine (CRBM).

13. The non-transitory computer-readable medium of claim 12, wherein applying the trained probabilistic model to the trial dataset corresponding to the randomized trial comprises using the CRBM to generate a set of samples of a target population.

14. The non-transitory computer-readable medium of claim 13, wherein the joint distribution is represented as:

$$p(y,h|x) = Z^{-1}(x)e^{-U(y,h|x)}$$

wherein:

y represents visible units of the CRBM, h represents hidden units of the CRBM, x represents feature units of the CRBM, Z(x) represents a normalization constant, and U(y, h|x) is the energy function; and the normalization constant is represented as:

$$Z(x) = \int dy \Sigma_H e^{-U(y,h|x)}.$$

15. The non-transitory computer-readable medium of claim 11, wherein a gradient that is used in the gradient descent is obtained from at least one of:

backpropagation; or automatic differentiation.

16. The non-transitory computer-readable medium of claim 12, wherein deriving, from the joint distribution, the energy function for the probabilistic model comprises summing over states of hidden units of the CRBM.

17. The non-transitory computer-readable medium of claim 11, wherein the measurement of regression accuracy is a minimum mean squared error prediction.

18. The non-transitory computer-readable medium of claim 11, wherein the approximation is a Laplace approximation.

19. The non-transitory computer-readable medium of claim 11, wherein a mode of the conditional distribution is identified by the point prediction model; and wherein the point prediction model comprises at least one selected from the group consisting of a linear model, a neural network, a decision tree, and a differential model.

20. The non-transitory computer-readable medium of claim 11, wherein the loss function is a negative log-likelihood function.

* * * * *